(12) United States Patent
Arevalo et al.

(10) Patent No.: US 9,804,158 B2
(45) Date of Patent: Oct. 31, 2017

(54) PEPTIDES AND METHODS FOR THE DETECTION OF LEISHMANIASIS

(71) Applicants: INSTITUT DE RECHERCHE POUR LE DEVELOPPEMENT, Marseilles (FR); UNIVERSIDAD PERUANA CAYETANO HEREDIA, Lima (PE)

(72) Inventors: Jorge Arevalo, Lima (PE); Eric Deharo, Auterive (FR); Angela Privat-Maldonado, Lima (PE)

(73) Assignees: Institut de Recherche pour le Développement, Marseilles (FR); Universidad Peruana Cayetano Heredia, Lima (PE)

( * ) Notice: Subject to any disclaimer, the term of this patent is extended or adjusted under 35 U.S.C. 154(b) by 0 days.

(21) Appl. No.: 14/902,234

(22) PCT Filed: Jul. 2, 2013

(86) PCT No.: PCT/IB2013/055423
§ 371 (c)(1),
(2) Date: Dec. 30, 2015

(87) PCT Pub. No.: WO2015/001383
PCT Pub. Date: Jan. 8, 2015

(65) Prior Publication Data
US 2016/0146809 A1 May 26, 2016

(51) Int. Cl.
*G01N 33/569* (2006.01)

(52) U.S. Cl.
CPC ... *G01N 33/56905* (2013.01); *G01N 2333/44* (2013.01); *G01N 2469/20* (2013.01)

(58) Field of Classification Search
None
See application file for complete search history.

(56) References Cited

FOREIGN PATENT DOCUMENTS

| ES | 2356439 A1 | * | 8/2011 |
| WO | 200181338 A1 | * | 11/2001 |
| WO | 2011/058137 A1 | | 5/2011 |
| WO | 2012/062861 A1 | | 5/2012 |

OTHER PUBLICATIONS

Alvar, J., et al., "Canine Leishmaniasis," Advances in Parasitology 57:1-88, Jan. 2004.
Requena, J.M., et al., "Evolutionarily Conserved Proteins as Prominent Immunogens During Leishmania Infections," Parasitology Today 16(6): 246-250, Jun. 2000.
Soto, M., et al., "During Active Viscerocutaneous Leishmaniasis the Anti-P2 Humoral Response Is Specifically Triggered by the Parasite P Proteins," Clinical & Experimental Immunology 100(2):246-252, May 1995.
Soto, M., et al., "Mapping of the Linear Antigenic Determinants From the Leishmania infantum Histone H2A Recognized by Sera From Dogs With Leishmaniasis," Immunology Letters 48(3):209-214, Jan. 1995.
Soto, M., et al., "Multicomponent Chimeric Antigen for Serodiagnosis of Canine Visceral Leishmaniasis," Journal of Clinical Microbiology 36(1):58-63, Jan. 1998.
Soto, M., et al., "Searching Genes Encoding Leishmania Antigens for Diagnosis and Protection," Scholarly Research Exchange 36(1):1-25, Jan. 2009.
Soto, M., et al., "The Leishmania infantum Acidic Ribosomal Protein LiP2a Induces a Prominent Humoral Response In Vivo and Stimulates Cell Proliferation In Vitro and Interferon-Gamma (IFN-γ) Production by Murine Splenocytes," Clinical & Experimental Immunology 122(2):212-218, Nov. 2000.
International Search Report dated Mar. 21, 2014, issued in corresponding International Application No. PCT/IB2013/055423, filed Jul. 2, 2013, 6 pages.

* cited by examiner

*Primary Examiner* — Jennifer Graser
(74) *Attorney, Agent, or Firm* — Christensen O'Connor Johnson Kindness PLLC

(57) ABSTRACT

The present invention relates to peptides and methods for the detection of anti-leishmanial antibodies in individuals suspected of infection with the protozoan parasite of the genus *Leishmania*, especially infection with a South American strain causing the American Tegumentary Leishmaniasis (ATL).

3 Claims, 2 Drawing Sheets

PEPTIDES AND METHODS FOR THE DETECTION OF LEISHMANIASIS

Figure 1:
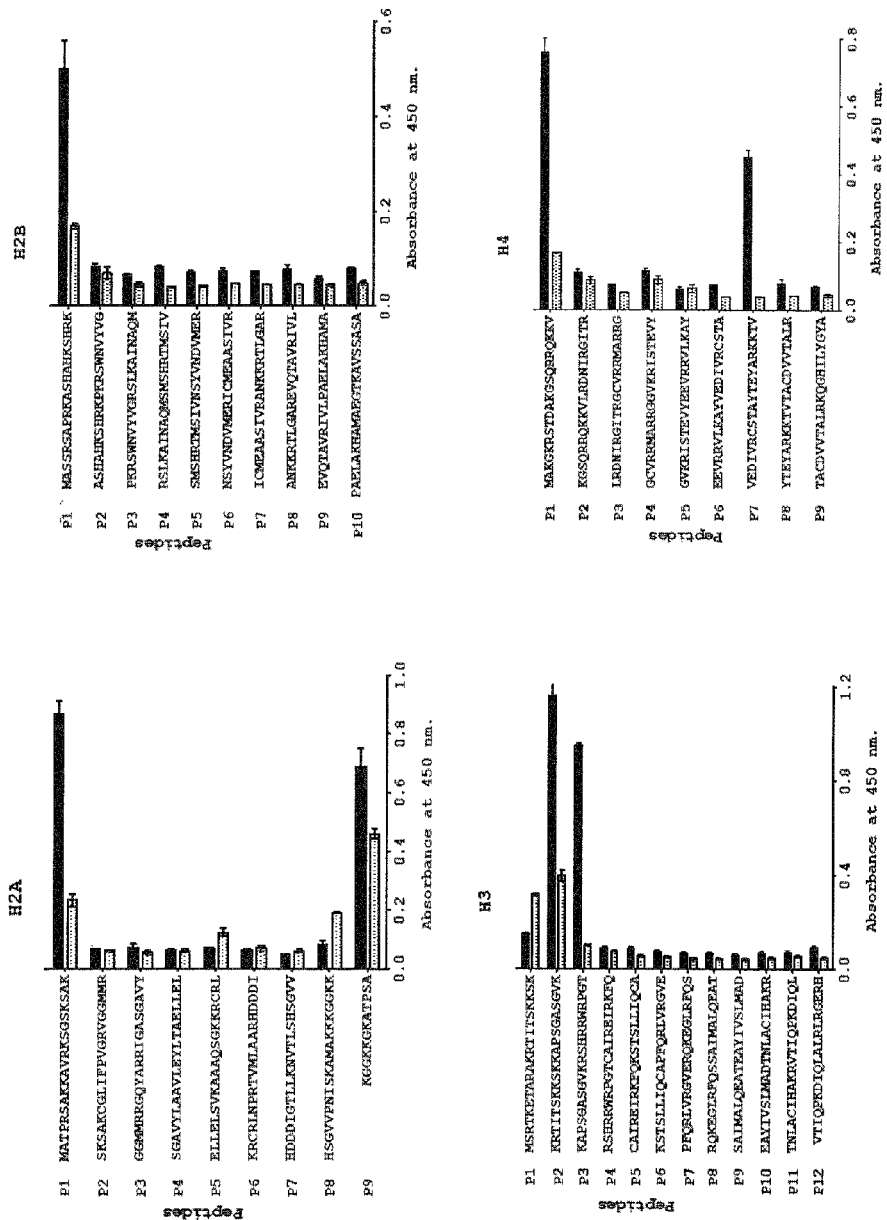

The present invention relates to peptides and methods for the detection of anti-leishmanial antibodies in individuals suspected of infection with the protozoan parasite of the genus *Leishmania*, especially infection with a South American strain causing the American Tegumentary Leishmaniasis (ATL).

Leishmaniasis comprises a heterogeneous group of diseases caused by intracellular protozoan parasites of the genus *Leishmania* that are widespread in 88 endemic countries, with an estimated annual incidence of 2 million cases [1].

*Leishmania* organisms are intracellular protozoan parasites of macrophages that cause a wide range of clinical diseases in humans and domestic animals, primarily dogs. The life cycles of *Leishmania* involve a vertebrate host (e.g., a human) and a vector (a sand fly) that transmits the parasite between vertebrate hosts. In the vector, the parasite takes on a characteristic morphological form known as the promastigote, and reproduces asexually in the vector's gut. When the vector bites a vertebrate host, promastigotes are injected into the host. The promastigotes then enter cells of the vertebrate host and change into a form known as the amastigote. The amastigote reproduces in the host's cells and, when the cells eventually die, the amastigotes are released and infect other cells. The symptoms and pathology associated with leishmaniasis result from the amastigotes killing the host's cells.

In South America, the most common form of the disease is the cutaneous leishmaniasis (CL), while mucosal Leishmaniasis (ML) and visceral Leishmaniasis (VL) are much less prevalent [2]. The CL and ML clinical manifestations although not fatal, can cause significant morbidity, social consequences and psychological traumas in affected people due to stigmatizing scars. VL, the most severe form of the disease, is less prevalent in the region [3].

The diagnostic of the disease is carried out by a combination of clinical, epidemiological, parasitological and immunological tests. Giemsa staining of biopsy smears is the most common method employed in rural endemic areas with a sensitivity ranging from 20% to 95% [4-6]. Parasite culture in NNN medium can achieve 54% of sensitivity, but bacterial and fungal contamination is frequent, affecting the success of the culture [6-9]. Furthermore, the sensitivity will vary according to the parasite load, sample collection and technical expertise.

Molecular diagnosis such as PCR, while more specific and sensitive, is also more expensive and requires more expertise than conventional procedures [4, 5, 10].

Serological diagnostic method for CL has been pursued in the past using whole parasite extracts; unfortunately, differences in parasite strains, antigen preparation and antigenic characteristics make them inappropriate for the development of standardized serodiagnostic methods [11-15].

Other studies report the use of recombinant proteins due to the variety of antigenic determinants they contain [16-20]; nevertheless, they might include crossreactive epitopes, which in turn compromise the test specificity [21].

A new improvement for the serodiagnosis of several diseases is the use of synthetic peptides, which might boost the sensitivity and specificity of the ELISA test [22, 23].

Histones and acidic ribosomal proteins (ARP) from *L. infantum* have been previously identified as antigenic proteins by canine VL sera [24] and their linear B cell epitopes were mapped on the most divergent regions of the proteins [18, 24-28]. Nevertheless, these experiments were carried out only with canine samples and only one study with a limited number of human ML sera was done with P2a and P2b [29]. Only one study has been performed with human CL and MCL serum samples, using synthetic peptides to explore the amino terminal region of the *L. braziliensis* ribosomal protein L25 with unsuccessful results [30], the existence of candidate diagnostic epitopes for serodiagnosis of human CL is still unknown.

There thus remains a need in the art for a rapid and effective diagnostic test for cutaneous leishmaniasis that may be readily employed in a field situation.

Inventors have conducted a large study of the linear epitopes of histones and acidic ribosomal proteins from *L. infantum*, a total of 75 synthetic peptides were screened, and they identified short peptides that are recognized by CL sera.

Subsequently, these immunodominant peptides were assessed on their diagnosis efficacy with a panel of CL sera; based on their advanced clinical knowledge of the American Tegumentary Leishmaniasis, Inventors have defined two levels of criteria to be applied for selecting the most appropriate peptide(s) for the diagnosis of CL (see examples), they then selected two specific peptides, H2A-P9 and P2a-P6, and designed an improved diagnostic test that allows a very accurate and sensitive diagnostic of South American *Leishmania* strains causing American Tegumentary Leishmaniasis.

Inventors have demonstrated that an indirect ELISA test using the peptides H2A-P9 and P2a-P6 can discriminate positive CL from negative sera for leishmaniasis. The obtained diagnostic parameters of this test demonstrate good effectiveness when taken to the clinical settings in endemic areas (see examples).

The present invention is thus directed to the selection and the combination of two specific immunodominant peptides from *L. infantum*: H2A-P9 of sequence KGGKKGKATPSA (SEQ. ID. No 9) and P2a-P6 of sequence AGAGAGAVAE-AKKEEPEEEE (SEQ. ID. No 67) for use in a method of diagnostic.

Consequently, the present invention provides a method of using those two peptides for the detection of anti-leishmanial antibodies present in the serum of patient suffering from cutaneous Leishmaniasis or muco-cutaneous Leishmaniasis provoked by infestation of South American Leishmaniasis strain. South American *Leishmania* strains comprise strains from the *Viannia* group (*L. (Viannia) braziliensis*, *L. (Viannia) panamensis*, *L. (Viannia) peruviana*, *L. (Viannia) guyanensis*, *L. (Viannia) lainsoni*, *L. (Viannia) colombiensis*) and strains from the *Leishmania* group (*L. (Leishmania) amazonensis*, *L. (Leishmania) garnhami*, L *(Leishmania) infantum*, *L. (Leishmania) mexicana*, *L. (Leishmania) pifanoi*, *L. (Leishmania) venezuelensis*); the present is preferably directed to the diagnosis of Leishmaniasis provoked by infestation with *L. braziliensis, L. mexicana, L. major, L. amazonensis* or *L. infantum*; these disorders are also called American Tegumentary Leishmaniasis.

The present invention further provides a diagnostic kit comprising the two peptides of SEQ. ID. No 9 and of SEQ. ID. No 67, said kit being useful for detecting anti-leishmanial antibodies present in the serum of patient suffering from cutaneous Leishmaniasis or muco-cutaneous Leishmaniasis provoked by infestation of South American *Leishmania* strain, more particularly *L. braziliensis, L. mexicana, L. major, L. amazonensis* or *L. infantum*; or American Tegumentary Leishmaniasis.

The diagnostic parameters of the method according to the present invention when applied to the serodiagnosis of CL have demonstrated to be comparable to those obtained for PCR in terms of sensitivity (S) and positive predictive value (PPV) [4]. The sensitivity of this technique is comparable to PCR (97%) and far better than microscopy smears observation (49%) or conventional parasite culture (58%) for CL diagnosis [43-45]. In comparison with serological methods like ELISA, IFAT and Western Blot using crude antigens from L. braziliensis, L. major or L. amazonensis, the method here described renders comparable or better diagnostic results [11, 12].

In the specific case of CL, accuracy negative predictive value (NPV) appears to be particularly important because an accurate negative diagnosis prevents the administration of pentavalent antimonials for 20 days, which is painful and potentially toxic to individuals with skin ulcers resembling leishmaniasis lesions [42].

Furthermore, a correct differential diagnosis will contribute to reduce disease burden of patients who must travel long distances to be treated.

Finally, compared with the classic diagnostic methods employed in rural areas like Leishmanin Skin Test, smears and traditional parasite culture in NNN medium, the present method demonstrated an improved performance, rendering high NPV and S values [48].

Considering the ease to manufacture synthetic peptides compared to recombinant proteins or isolated crude extract proteins, the present invention allows the development of new serological diagnostic reagents at low costs and amenable to be subjected to quality control assessment.

The present invention also allows the design of laboratory diagnostic tools that can be applied in primary health settings that use ELISA diagnosis for routine diagnosis.

A first object of the present invention is an in vitro diagnostic method for the detection of the presence or absence of antibodies indicative of a South American Leishmania strain responsible for the American Tegumentary Leishmaniasis, which bind to a peptide selected in the group consisting of H2A-P9 (SEQ. ID. No 9) and P2a-P6 (SEQ. ID. No 67) to form an immune complex, comprising the steps of:

a) contacting said peptides H2A-P9 (SEQ. ID. No 9) and P2a-P6 (SEQ. ID. No 67) with a biological sample for a time and under conditions sufficient to form an immune complex; and b) detecting the presence or absence of the immune complex formed in a).

The sequences of the peptides used in the diagnostic method according to the present invention are:

H2A-P9:
(SEQ. ID. No 9)
KGGKKGKATPSA
and

P2a-P6:
(SEQ. ID. No 67)
AGAGAGAVAEAKKEEPEEEE.

These peptides have been identified from the strain L. infantum with the method described in the examples. They may be prepared and isolated by well known techniques, such as solid phase synthesis [41].

In one embodiment of the present invention, the in vitro diagnostic method makes use of isolated synthetic peptides of sequence SEQ. ID. No 9 and SEQ. ID. No 67.

These peptides may be each in separate containers or mixed in the same container; optionally they are immobilized on an appropriate support like the lateral flow format.

In this device, the diagnostic peptide is immobilized on membrane, such as a Polyvinylidene fluoride or a nitrocellulose membrane.

For detection purpose, anti human IgG labelled with a signal generator (substrate chromogen or colloidal gold) is deposited on a glass fiber strip (sample application pad); when a solution of serum to be tested is applied on the pad, it dissolves the labelled reporter and this binds to all antibodies in the sample. This mixture is then transported by capillarity (chromatography principle) into the next membrane containing the diagnostic peptide.

If antibodies against the diagnostic peptide are present, they bind to the diagnostic peptide striped on the membrane generating a signal. An additional antibody specific to the colloidal labelled antibody is used to produce a control signal.

It should be implicit by one of expert in the art, that any conventional protein assay formats, particularly immunoassay formats, may be designed to use the selected peptides herein for the detection of Leishmania infection. This invention is thus not limited by the selection of the particular assay format, and is believed to encompass assay formats that are known to those of skill in the art.

Reagents for ELISA or other immunodetection assays can be provided in the form of kits. In one embodiment, a kit contains a mixture of suitable peptides or means for preparing such mixtures, and/or reagents for detecting peptide-antibody complexes. A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom. The term "biological sample" encompasses a clinical sample, and also includes cells in culture, cell supernatants, cell lysates, serum, plasma, biological fluid, and tissue samples.

The most common technique for conducting step b) is the Enzyme-linked immunosorbent assay (ELISA). It involves at least one antibody with specificity for a particular antigen, in our case the peptides immobilized on a solid support (usually a polystyrene microtiter plate or a dip-stick) via adsorption to the surface or more specifically (via capture by another antibody specific to the same antigen, in a "sandwich" ELISA). The detection antibody (the sample) is added, forming a complex with the peptide. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are not specifically bound. After the final wash step, the plate is developed by adding an enzymatic substrate to produce a visible signal, which indicates the quantity of antigen in the sample.

According to a particular embodiment, if the result of the in vitro diagnostic method is uncertain, additional steps may be added to test again the serum with peptide H2A-P9 to increase accuracy and sensitivity, said additional steps comprise:

c) contacting said biological sample with the peptide H2A-P9 of sequence KGGKKGKATPSA (SEQ. ID. No 9) and d) detecting the presence or absence of the immune complex formed in c).

The present invention also provides a diagnostic kit for detecting anti-leishmanial antibodies present in the serum of patient suffering from American Tegumentary Leishmaniasis wherein said diagnostic kit comprises the two peptides of SEQ. ID. No 9 and of SEQ. ID. No 67.

The kit can include microtiter plates to which the peptide (s) of the invention have been pre-adsorbed, another appropriate assay device, various diluents and buffers, labelled conjugates or other agents for the detection of specifically bound antigens or antibodies, and other signal-generating reagents, such as enzyme substrates, cofactors and chromogens. Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex.

The diagnostic kit preferably comprises: the two peptides of SEQ. ID. No 9 and of SEQ. ID. No 67; reagent(s) to detect polypeptide-antibody immune complex; optionally a biological reference sample lacking antibodies that immunologically bind with said peptides; and optionally a comparison sample comprising antibodies which can specifically bind to said peptides; wherein said peptides, reagent(s), biological reference sample, and comparison sample are present in an amount sufficient to perform said detection.

In a particular embodiment, the diagnostic kit consists of ELISA kit; preferably, the ELISA kit comprises the H2A-P9 (SEQ. ID. No 9) and P2a-P6 (SEQ. ID. No 67) pre-coated ELISA plates, positive control, negative control, acceptable diluents, enzyme conjugated anti-human IgG, for example, Anti-Human IgG (H&L) in goat conjugate (peroxydase, phosphatase) (see also http://www.polysciences.com/Core/Display.aspx?pageId=98&categoryId=158&productId=1518), substrate chromogen (examples for peroxidise: 3,3-dimethoxybenzidine, O- -dianisidine (ODN) turns reddish; 3,3-Diaminobenzidine turns reddish; 3-amino-9-ethyl carbazole turns reddish; 4-Chloro-1-naphtol turns bluish; and for alkaline phosphatise: 5-bromo-4-chloro-3-indolyl phosphate (BCIP) turns bluish or nitro blue tetrazolium (NBT) turns bluish), substrate buffer and an instruction manual to use the kit.

The diagnostic kit may be in the form of a Dipstick which may be dipped in several wells each comprising biological sample, and reagents.

FIG. 1 represents four graphs that show the reactivity of the CL (open bars) and MCL (solid bars) sera against the synthetic peptides, 20-mer overlapping by five residues (H2A) and ten residues (H2B, H3, H4), covering the entire sequence of the proteins. The OD450 mean values of a pool of two to six sera against each one of the peptides are represented. Sera were used at a dilution of 1:150. The amino acid sequences of the synthetic peptides are provided in the Sequence Listing along with their respective sequence identifiers.

Figure 2:
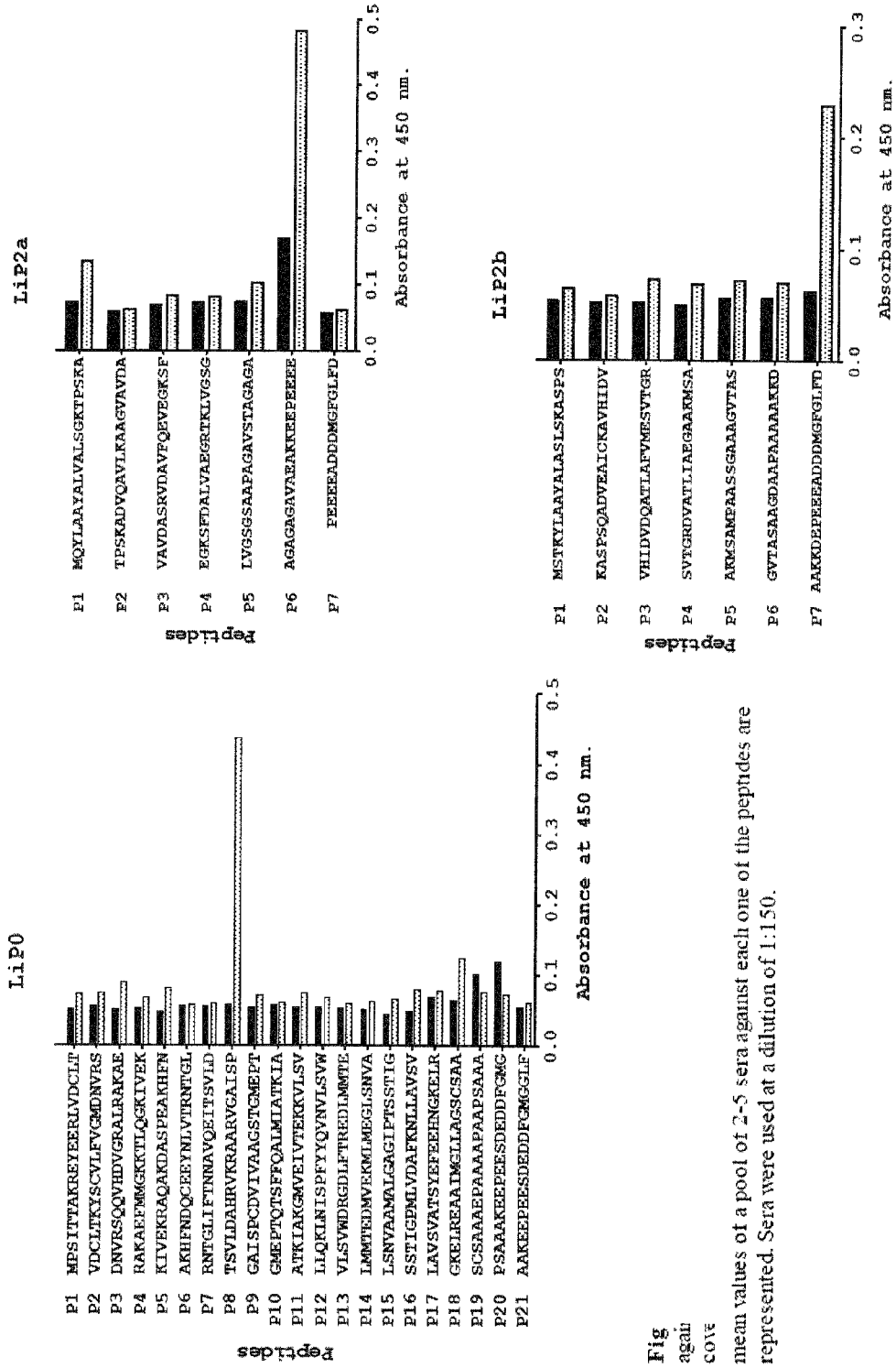

FIG. 2 represent four graphs that show the reactivity of the CL (open bars) and MCL (solid bars) sera against the synthetic peptides, 20-mer overlapping by five residues, covering the entire sequence of LiP2a, LiP2b and P0. The OD450 mean values of a pool of two to six sera against each one of the peptides are represented. Sera were used at a dilution of 1:150. The amino acid sequences of the synthetic peptides are provided in the Sequence Listing along with their respective sequence identifiers.

The present invention will be more readily understood by referring to the following example. This example is illustrative of the wide range of applicability of the present invention and is not intended to limit its scope. Modifications and variations can be made therein without departing from the spirit and scope of the invention. Although any method and material similar or equivalent to those described herein can be used in the practice for testing of the present invention, the preferred methods and materials are described.

EXAMPLE 1—IDENTIFICATION OF IMMUNODOMINANT PEPTIDES FROM L. INFANTUM HISTONES AND ARP

I.A. Methods

I.A.1. Human Sera

The serum samples used were divided into three groups:

Group I: Sera from twenty ML and twenty one CL patients were obtained from the bank of sera of the Microbiology Laboratory, Faculty of Biology, San Antonio Abad University of Cuzco, Peru. All samples were reactive to at least one conventional laboratory test for ATL, such as parasite culture, IFA or microscopy. This group was tested against recombinant histones and ARP and two to five hyper reactive sera from each clinical manifestation were pooled for epitope mapping.

Group II: Sera from fifteen CL, ten negative endemic controls (NEC) from Cusco, Peru were obtained from the bank of sera of FP7 RAPSODI Project. Samples from patients with Chagas (7) and Sporotrichosis (6) from Lima, Peru were also included. These samples were individually tested against the selected ten synthetic peptides.

Group III: Eighteen CL and thirteen NEC sera from the bank of sera of the FP7 RAPSODI Project were individually assayed with the two diagnostic candidate epitopes.

I.A.2. Epitope Mapping

For the epitope mapping, a library of overlapping peptides covering the whole sequence of the L. infantum LiH2A, LiH2B, LiH3, LiH4, LiP0, LiP2a and LiP2b was employed The screening was carried out with a pool of sera obtained from ATL patients.

Peptides were synthesized by the simultaneous multiple-peptide solid-phase synthetic method using a polyamide resin and FMOC chemistry [41]. Purity was checked by amino acid analysis and HPLC. For LiH2A [26], LiH3 [27], LiP2a and LiP2b [25], and LiP0 [28] peptides overlapped by 5 amino acids. For LiH2B and LiH4, peptides overlapped by 10 amino acids [24]. A total of 75 peptides were assayed, all peptides were 20-mer long, except H2A-P9 (12-mer), P2a-P7 (16-mer), H3-P12 (19-mer) and H2B-P10 and P2b-P7 (21-mer).

I.A.3. ELISA Measurements

To select both the most reactive sera against recombinant antigens and to carry out the epitope mapping, sera from Group I were tested using the Falcon assay screening test-enzyme-linked immunosorbent assay (FAST-ELISA; Becton Dickinson) [27].

The antigen concentration for recombinant proteins was 2 μg/ml and 100 μg/ml for synthetic peptides. Antigen-coated lids were incubated for 1 h with the blocking solution and pools of the most reactive two to six serum samples for each recombinant protein were used for the epitope mapping.

Serum samples were diluted 1:200 for recombinant proteins and 1:150 for synthetic peptides in blocking solution and incubated for 2 h at room temperature with shaking. As secondary antibody, horseradish peroxidase-labelled anti- IgG antibodies (dilution 1:2000, Nordic Immunology) were used. After 1 h of incubation at room temperature, lids were washed and the immune complexes were revealed with orthophenylenediamine as the chromogenic substrate. Absorbance was read at 450 nm.

I.B. Results—B-Cell Epitope Mapping Using Synthetic Peptides

To select the most reactive serum samples from a panel of CL and ML sera corresponding to Group I, recombinant proteins were individually tested (data not shown). It was possible to combine at least 3 sera for the epitope mapping of H2A, H2B, H4, P0 and P2b. For P2a and H3 only two sera were pooled for ML and CL respectively. A collection of synthetic peptides spanning the whole protein sequences, were tested by FAST-ELISA, with exception of LiP0 protein, where positions between 170 and 180 were not available.

Peptides located at the N-terminal region of histones (H2A-P1, H2B-P1, H3-P2, H3-P3, H4-P1), at the C-terminal region of LiH2A (H2A-P9), LiP2a (P2a-P6) and LiP2b (P2b-P7) and at the middle of LiH4 (H4-P7) and LiP0 (P0-P8) demonstrated to be immunodominant (FIGS. 1 to 7). A total of ten linear epitopes were selected like peptide candidates for the determination of their diagnostic value: H2A-P1 (SEQ. ID. No 1), H2A-P9 (SEQ. ID. No 9), H2B-P1 (SEQ. ID. No 10), H3-P2 (SEQ. ID. No 21), H3-P3 (SEQ. ID. No 22), H4-P1 (SEQ. ID. No 32), H4-P7 (SEQ. ID. No 38), P0-P8 (SEQ. ID. No 48), P2a-P6 (SEQ. ID. No 67) and P2b-P7 (SEQ. ID. No 75).

II.A. Method

Ten immunodominant peptides, selected after the epitope mapping were provided by Bio-Synthesis, Inc. (612 East Main Street Lewisville, Tex. 75057, USA). Peptides were further analyzed using conventional ELISA following the conditions described above and sera from Group II. After the selection of the two diagnostic candidate peptides, they were analyzed using serum samples from Group III. All samples were processed in duplicates.

Cut-off values were defined by the area under the receiver-operating characteristic curve.

Statistical Analysis

The results obtained for each serum sample tested were used to construct 2×2 contingency tables where the sera were further classified according to the disease's presence or absence, as positive or negative.

II.B. Results

Results are presented in Table 1 below.

| | CL | | NEGATIVE CONTROLS | | OTHER PATHOLOGIES | | | | Others pathologies combined | | All no Leishmaniasis sera | |
|---|---|---|---|---|---|---|---|---|---|---|---|---|
| | | | | | Chagas | | Sporotrichosis | | | | | |
| | | | | | Number of samples tested | | | | | | | |
| | 15 | | 10 | | 7 | | 6 | | 13 | | 23 | |
| | % | N. positives | % | N. positives | % | N. positives | % | N. positives | % | N. positives | % | N. positives |
| H2A-P1 | 60.00 | 9 | 10.00 | 1 | 42.86 | 3 | 66.67 | 4 | 53.85 | 7 | 34.78 | 8 |
| H2A-P9 | 73.33 | 11 | 0.00 | 0 | 0.00 | 0 | 16.87 | 1 | 7.69 | 1 | 4.35 | 1 |
| H2B-P1 | 93.33 | 14 | 20.00 | 2 | 14.29 | 1 | 33.33 | 2 | 23.08 | 3 | 21.74 | 5 |
| H3-P2 | 80.00 | 12 | 10.00 | 1 | 28.57 | 2 | 16.67 | 1 | 23.08 | 3 | 17.39 | 4 |
| H3-P3 | 46.67 | 7 | 30.00 | 3 | 28.57 | 2 | 33.33 | 2 | 30.77 | 4 | 30.43 | 7 |
| H4-P1 | 66.67 | 10 | 20.00 | 2 | 28.57 | 2 | 66.67 | 4 | 46.15 | 6 | 34.78 | 8 |
| H4-P7 | 60.00 | 9 | 30.00 | 3 | 0.00 | 0 | 16.67 | 1 | 7.69 | 1 | 17.39 | 4 |
| P0-P8 | 66.67 | 10 | 10.00 | 1 | 0.00 | 0 | 0.00 | 0 | 0.00 | 0 | 4.35 | 1 |
| P2a-P6 | 80.00 | 12 | 0.00 | 0 | 14.29 | 1 | 0.00 | 0 | 7.69 | 1 | 4.35 | 1 |
| P2b-P7 | 86.67 | 13 | 50.00 | 5 | 71.43 | 5 | 0.00 | 0 | 38.46 | 5 | 43.48 | 10 |

EXAMPLE 2—ASSESSMENT OF THE DIAGNOSTIC VALUE OF PEPTIDE CANDIDATES: INDIVIDUAL ASSAY OF PEPTIDE CANDIDATES

The ten selected peptides were tested with serum samples from Group II to confirm their highly antigenic nature; their potential interest for diagnostic purpose has been evaluated using a first set of diagnostic parameters defined by Inventors. Considering that the diagnostic test needs to be sensitive and with a minimal rate of false positive because false positive will lead to the application of unnecessary treatment which is costly, risky and painful, peptides recognized by more than 70% of CL sera and with less than 15% of cross-reactivity were arbitrarily considered as potential diagnostic candidates.

Under these criteria, peptides H2A-P9 and P2a-P6 were selected.

II.C. Confirmation of the Diagnostic Value of Peptides H2A-P9 and P2a-P6

The purpose is here to confirm that the use of the combination of the two selected peptides H2A-P9 and P2a-P6 allows a very reliable diagnostic of American Tegumentary Leishmaniasis.

Diagnostic parameters used to describe the accuracy of the diagnostic test were calculated; they included:
  accuracy: number and proportion of all the observations in the table which have been classified correctly by the test;
  kappa: this parameter takes on the value 1 if there is perfect agreement; i.e. the test always correctly predicts the outcome (1 perfect, >0.75 excellent, 0.4-0.75 fair, <0.4 poor).
  Kappa is a measure of agreement and takes on the value zero if there is no more agreement between test and outcome then can be expected on the basis of chance.

Kappa takes on the value 1 if there is perfect agreement; i.e. the test always correctly predicts the outcome. It is considered that Kappa values lower than 0.4 represent poor agreement, values between 0.4 and 0.75 fair to good agreement, and values higher than 0.75 excellent agreement. Negative Kappa indicates a problem in the application of the test. Kappa is dependent not only on the quality of the test, i.e., the inside of the table, but also on the prevalence of the disease in the population in which the test is applied, kappa is also sensitive to the distribution of cases in the table margin. Basically what Kappa shows is that for the same sensitivity and specificity the agreement between test and outcome will decrease with a decreasing prevalence. In Kappa terms a test will perform worse in low prevalence populations.

Mode of Calculation:

$$\text{Kappa} = \frac{(\text{Observed agreement} - \text{expected agreement})}{1 - \text{expected agreement}}$$

$$\left(\text{see http://epiville.ccnmtl.columbia.edu/popup/how\_to\_calculate\_kappa.html}\right)$$

sensitivity (S): it is the probability that an individual which is diseased is indeed tested as diseased.

The level of sensitivity to be applied in a diagnostic test is defined taking into account the seriousness of the "disease" and the cost and availability of the treatment; i.e. the sensitivity of a test is to be high if the "disease" is relatively serious and the "cure" is relatively inexpensive and easily available.

specificity (E): it is the probability that an individual which is not diseased is tested as not diseased.

The level of specificity is usually high if the disease is not so serious and the "cure" is relatively expensive in money and other terms.

There is a tradeoff between specificity and sensitivity, high specificity mostly means low sensitivity, and vice versa.

positive predictive value (PPV): indicates how much more likely it is to get a positive test in the diseased as opposed to the non-diseased group.

negative predictive value (NPV): indicates how much more likely it is to get a negative test in the non-diseased as opposed to the diseased group.

diagnostic odds: this parameter is often used as a measure of the discriminative power of the test; it has the value one if the test does not discriminate between diseased and not diseased individuals. Very high values above one means that a test discriminates well. Values lower than one mean that there is something wrong in the application of the test.

error odds: this parameter indicates if the probability of being wrongly classified is highest in the diseased or in the non-diseased group. If the error odds is higher than one the probability is highest in the diseased group (and the specificity of the test is better than the sensitivity), if the value is lower than one the probability of an incorrect classification is highest in the non-diseased group (and the sensitivity of the test is better than the specificity).

Youden's J: this parameter is used to study the overall performance of a test; it takes on the value 1 if a diagnostic test discriminates perfectly and without making any mistakes. As a consequence, if the purpose is to minimize the probability of making an error, the Youden's J has to be maximized; that, of course, is of only theoretical importance, such decisions should be taken on the basis of a cost-benefit analysis of treatment as opposed to no treatment.

positive predictive accuracy: in a table representative of the population, this parameter gives: 1) the post-test probability, the probability for an individual in the population who tested positive of having the disease; 2) of those who tested positive the fractions who were correctly and who were not-correctly classified.

negative predictive accuracy: In a table representative of the population this parameter gives: 1) the post-test probability, the probability for an individual in the population who tested negative of not having the disease; 2) of those who tested negative the fractions who were correctly and who were not-correctly classified.

Based on the extended clinical experience of the American Tegumentary Leishmaniasis of the Inventors, they have selected the parameters, sensitivity and specificity and the two predictive accuracies (accuracy and kappa), that are considered as the most valuable of the indicators.

The threshold value for each peptide is 3 standard deviations of the value obtained when the peptides were tested with true negative control sera.

Sensitivity and specificity give a good view of the quality of the test relatively independent of circumstances. The predictive accuracies give a view of what happens in different practical situations in terms of numbers and proportions tested with correct and incorrect results. Predictive accuracies also give the post test probability of having the disease, an essential piece of information to communicate to the patient together with his or her test result.

Results

To determine the above-mentioned diagnostic parameters of H2A-P9 and P2a-P6, a new panel of serum samples is assayed (group III) and analyzed in combination with the results obtained for group II. All peptides showed high levels of specificity (>80%) but their individual sensitivity were below 80% (Table II). Nonetheless, when the results obtained for each of the three synthetic peptides were analyzed altogether, thirty one out of thirty three of confirmed CL patients were correctly diagnosed. This combination provided 94% sensitivity, 83% specificity, 84% PPV and 94% NPV.

| H2A-P9CT | H2A-P9 Ct + P2a-P6 Ct | P2a-P6 |
|---|---|---|
| Cases tested: 69 | Cases tested: 69 | Cases tested: 69 |
| 23 + 1 = 24 tested positive | 28 + 2 = 30 tested positive | 26 + 1 = 27 tested positive |
| 10 + 35 = 45 tested negative | 5 + 34 = 39 tested negative | 7 + 35 = 42 tested negative |
| 23 + 10 = 33 were positive | 28 + 5 = 33 were positive | 26 + 7 = 33 were positive |
| 1 + 35 = 36 were negative | 2 + 34 = 36 were negative | 1 + 35 = 36 were negative |
| True positives | True positives | True positives |

-continued

| H2A-P9CT | H2A-P9 Ct + P2a-P6 Ct | P2a-P6 |
|---|---|---|
| 23/69 = 0.333 | 28/69 = 0.406 | 26/69 = 0.377 |
| variance: 0.00322; Std. Err: 0.05675 | variance: 0.00349; Std. Err: 0.05911 | variance: 0.0034; Std. Err: 0.05834 |
| 95% Cl: 0.191 < Tp < 0.475 | 95% Cl: 0.258 < Tp < 0.554 | 95% Cl: 0.231 < Tp < 0.523 |
| Wilson Cl: 0.205 < Tp < 0.491 | Wilson Cl: 0.266 < Tp < 0.562 | Wilson Cl: 0.241 < Tp < 0.534 |
| True negatives | True negatives | True negatives |
| 35/69 = 0.507 | 34/69 = 0.493 | 35/69 = 0.507 |
| variance: 0.00362; Std. Err: 0.06019 | variance: 0.00362; Std. Err: 0.06019 | variance: 0.00362; Std. Err: 0.06019 |
| 95% Cl: 0.357 < Tn < 0.658 | 95% Cl: 0.342 < Tn < 0.643 | 95% Cl: 0.357 < Tn < 0.658 |
| Wilson Cl: 0.356 < Tn < 0.657 | Wilson Cl: 0.343 < Tn < 0.644 | Wilson Cl: 0.356 < Tn < 0.657 |
| False positives | False positives | False positives |
| 1/69 = 0.014 | 2/69 = 0.029 | 1/69 = 0.014 |
| variance: 0.00021; Std. Err: 0.01439 | variance: 0.00041; Std. Err: 0.0202 | variance: 0.00021; Std. Err: 0.01439 |
| 95% Cl: −0.021 < Fp < 0.05 | 95% Cl: −0.022 < Fp < 0.079 | 95% Cl: −0.021 < Fp < 0.05 |
| Wilson Cl: 0.001 < Fp < 0.119 | Wilson Cl: 0.004 < Fp < 0.141 | Wilson Cl: 0.001 < Fp < 0.119 |
| False negatives | False negatives | False negatives |
| 10/69 = 0.145 | 5/69 = 0.072 | 7/69 = 0.101 |
| variance: 0.0018; Std. Err: 0.04238 | variance: 0.00097; Std. Err: 0.03121 | variance: 0.00132; Std. Err: 0.03635 |
| 95% Cl: 0.039 < Fn < 0.251 | 95% Cl: −0.006 < Fn < 0.15 | 95% Cl: 0.011 < Fn < 0.192 |
| Wilson Cl: 0.064 < Fn < 0.289 | Wilson Cl: 0.022 < Fn < 0.2 | Wilson Cl: 0.037 < Fn < 0.237 |
| Accuracy | Accuracy | Accuracy |
| (23 + 35)/69 = 0.841 | (23 + 35)/69 = 0.899 | (26 + 35)/69 = 0.884 |
| variance: 0.00194; Std. Err: 0.04407 | variance: 0.00132; Std. Err: 0.03635 | variance: 0.00149; Std. Err: 0.03854 |
| 95% Cl: 0.73 < Acc < 0.951 | 95% Cl: 0.808 < Acc < 0.989 | 95% Cl: 0.788 < Acc < 0.98 |
| Wilson Cl: 0.695 < Acc < 0.926 | Wilson Cl: 0.763 < Acc < 0.963 | Wilson Cl: 0.746 < Acc < 0.954 |
| Kappa agreement measure = (58 − (2412/69))/ . . . /(69 − (2412/69)) = 0.677 | Kappa agreement measure = (62 − (2394/69))/ . . . /(69 − 94/69)) = 0.796 | Kappa agreement measure = (61 − (2403/69))/ . . . /(69 − (2403/69)) = 0.766 |
| variance = 0.01348; Std. Err: 0.1161 | variance = 0.01438; Std. Err: 0.11992 | variance = 0.01405; Std. Err: 0.11852 |
| 95% Cl: 0.387 < Kappa < 0.967 | 95% Cl: 0.496 < Kappa < 1.096 | 95% Cl: 0.47 < Kappa < 1.062 |
| Sensitivity | Sensitivity | Sensitivity |
| 23/33 = 0.697 | 23/33 = 0.848 | 26/33 = 0.788 |
| variance: 0.0064; Std. Err: 0.08 | variance: 0.0039; Std. Err: 0.06242 | variance: 0.00506; Std. Err: 0.07116 |
| 95% Cl: 0.497 < Sens < 0.897 | 95% Cl: 0.692 < Sens < 1.005 | 95% Cl: 0.61 < Sens < 0.966 |
| Wilson Cl: 0.465 < Sens < 0.862 | Wilson Cl: 0.622 < Sens | Wilson Cl: 0.557 < Sens < 0.921 |
| Specificity | Specificity | Specificity |
| 35/36 = 0.972 | 34/36 = 0.944 | 35/36 = 0.972 |
| variance: 0.00075; Std. Err: 0.02739 | variance: 0.00146; Std. Err: 0.03818 | variance: 0.00075; Std. Err: 0.02739 |
| 95% Cl: 0.904 < Spec < 1.041 | 95% Cl: 0.849 < Spec < 1.04 | 95% Cl: 0.904 < Spec < 1.041 |
| Wilson Cl: 0.904 < Spec < 0.999 | Wilson Cl: 0.75 < Spec < 0.993 | Wilson Cl: 0.788 < Spec < 0.999 |
| Positive Likelihood | Positive Likelihood | Positive Likelihood |
| 0.697/(1 − 0.972)) = 25.091 | 0.848/(1 − 0.944)) = 15.273 | 0.788/(1 − 0.972)) = 28.364 |
| 95% Cl: 2.098 < PL < 300.121 | 95% Cl: 2.714 < PL < 85.957 | 95% Cl: 2.386 < PL < 337.128 |
| Negative Likelihood | Negative Likelihood | Negative Likelihood |
| (1 − 0.697)/0.972 = 0.312 | (1 − 0.848)/0.944 = 0.16 | (1 − 0.788)/0.972 = 0.218 |
| 95% Cl: 0.16 < NL < 0.605 | 95% Cl: 0.057 < NL < 0.452 | 95% Cl: 0.094 < NL < 0.506 |
| Diagnostic Odds | Diagnostic Odds | Diagnostic Odds |
| 0.697/(1 − 0.697))/(0.972/(1 − 0.972) = 80.5 | 0.848/(1 − 0.848))/(0.944/(1 − 0.944) = 95.2 | 0.788/(1 − 0.788))/(0.972/(1 − 0.972) = 130 |
| variance: 7595.175; Std. Err: 87.1503 | variance: 6934.368; Std. Err: 83.27285 | variance 20447.14286; Std. Err: 142.99351 |
| 95% Cl: −137.376 < Dor < 298.376 | 95% Cl: −112.982 < Dor < 303.382 | 95% Cl: −227.484 < Dor < 487.484 |
| Wald's Cl: 5.375 < Eor < 1205.667 | Wald's Cl: 10.689 < Eor < 847.904 | Wald's Cl: 8.312 < Eor < 2033.288 |
| Error Odds | Error Odds | Error Odds |
| 0.697/(1 − 0.697))/(0.972/(1 − 0.972) = 0.066 | 0.848/(1 − 0.848))/(0.944/(1 − 0.944) = 0.329 | 0.788/(1 − 0.788))/(0.972/(1 − 0.972) = 0.106 |
| variance: 0.00506; Std. Err: 0.07114 | variance: 0.08303; Std. Err: 0.28814 | variance: 0.01363; Std. Err: 0.11673 |
| 95% Cl: −0.112 < Eor < 0.244 | 95% Cl: −0.391 < Eor < 1.05 | 95% Cl: −0.186 < Eor < 0.398 |
| Wald's Cl: 0.004 < Eor < 0.984 | Wald's Cl: 0.037 < Eor < 2.934 | Wald's Cl: 0.007 < Eor < 1.66 |
| Youden's J | Youden's J | Youden's J |
| 0.972 + 0.697 − 1 = 0.669 | 0.944 + 0.848 − 1 = 0.793 | 0.972 + 0.788 − 1 = 0.76 |
| variance: 0.00715; Std. Err: 0.08456 | variance: 0.00535; Std. Err: 0.07317 | variance: 0.00581; Std. Err: 0.07625 |
| 95% Cl: 0.458 < J < 0.881 | 95% Cl: 0.61 < J < 0.976 | 95% Cl : 0.569 < J < 0.951 |
| Prevalence = (23 + 10)/69 = 0.478 | Prevalence = (28 + 5)/69 = 0.478 | Prevalence = (26 + 7)/69 = 0.478 |
| variance: 0.00362; Std. Err: 0.06014 | variance: 0.00362; Std. Err: 0.06014 | variance: 0.00362; Std. Err: 0.06014 |

| H2A-P9CT | H2A-P9 Ct + P2a-P6 Ct | P2a-P6 |
|---|---|---|
| 95% CI: 0.328 < Pr < 0.629 | 95% CI: 0.328 < Pr < 0.629 | 95% CI : 0.328 < Pr < 0.629 |
| Wilson CI: 0.33 < Pr < 0.631 | Wilson CI: 0.33 < Pr < 0.631 | Wilson CI: 0.33 < Pr < 0.631 |
| Positive predictive accuracy 23/24 = 0.958 | Positive predictive accuracy 28/30 = 0.933 | Positive predictive accuracy 26/27 = 0.963 |
| variance: 0.00166; Std. Err: 0.04079 | variance: 0.00207; Std. Err: 0.04554 | variance: 0.00132; Std. Err: 0.03634 |
| 95% CI: 0.856 < pp < 1.06 | 95% CI: 0.819 < pp < 1.047 | 95% CI: 0.872 < pp < 1.054 |
| Wilson CI: 0.705 < pp < 0.999 | Wilson CI: 0.709 < pp < 0.992 | Wilson CI: 0.731 < pp < 0.999 |
| Negative predictive accuracy 35/45 = 0.778 | Negative predictive accuracy 34/39 = 0.872 | Negative predictive accuracy 35/42 = 0.833 |
| variance: 0.00384; Std. Err: 0.06197 | variance: 0.00287; Std. Err: 0.05353 | variance: 0.00331; Std. Err: 0.05751 |
| 95% CI: 0.623 < np < 0.933 | 95% CI: 0.738 < np < 1.006 | 95% CI: 0.69 < np < 0.977 |
| Wilson CI: 0.583 < np < 0.9 | Wilson CI: 0.671 < np < 0.962 | Wilson CI : 0.636 < np < 0.938 |
| Chi squares (All with 1 degree of freedom): | Chi squares (All with 1 degree of freedom): | Chi squares (All with 1 degree of freedom): |
| Pearson's = 33.989 (p = 0) | Pearson's = 44.05 (p = 0) | Pearson's = 41.763 (p = 0) |
| LRX = 39.536 (p = 0) | LRX = 50.957 (p = 0) | LRX = 49.123 (p = 0) |
| Yate's = 31.103 (p = 0) | Yate's = 40.883 (p = 0) | Yate's = 38.633 (p = 0) |
| M-Haenszel = 33.497 (p = 0) | M-Haenszel = 43.412 (p = 0) | M-Haenszel = 41.158 (p = 0) |
| Pearson's correlation: 0.70185 | Pearson's correlation: 0.79901 | Pearson's correlation: 0.77799 |

EXAMPLE 3—DIAGNOSTIC TEST FOR NEW WORLD LEISHMANIASIS (IgG)

Materials: The ELISA Kit to measure anti-*Leishmania* IgG contains components required to perform an enzyme-linked immunoassay for the specific measurement of human IgG. Sufficient quantities of reagents are provided to yield 4 plates of 96 wells if there commended assay procedure and recommended storage and handling of materials are followed as specified on this insert.
Control: Human Serum Control (Monoclonal)
Form: Liquid, 1 vial×0.2 mL; Storage: Prolonged store at or below −20° C.
Use: Gently agitate to dissolve completely prior to use.
Human Serum
Control is diluted in glycerol [1/2] and the recommended working dilution is 1/150 in Blocking Buffer.
Secondary Antibody: Horseradish Peroxidase Anti-Human IgG
Form: Powder, 1 vial×0.3 mg; Storage: Lyophilized conjugate may be stored at +4° C.; prolonged storage at or below −20° C.
Use: Reconstitute reagent by adding 0.1 ml sterile distilled water; dissolve it and add an equal volume of glycerol (final concentration of 0.5 mg/ml). Divide into small aliquots, freeze and store at or below −20° C. Prior to use, an aliquot is thawed slowly at ambient temperature and used to prepare working dilutions by adding Blocking Buffer at a ratio of 1:200. Do not prepare more diluted Anti-Human IgG solution than is needed. Repeated thawing and freezing should be avoided. Working dilutions should be stored at +4° C., not refrozen, and preferably used the same day.
Chromogen: OPD Tablets from Sigma Cod. P6662
Form: 33 OPD Tablets, 1 mg each; Storage: Store tablets at 2-8° C. Protect from heat, light and moisture. Allow to reach room temperature 10 minutes before use.
Use: Dissolve one tablet in 2.5 ml of 0.05M phosphate-citrate buffer, pH 5.0 to a final concentration of 0.4 mg/ml to prepare the Developing Solution. Add 1 µL of fresh 30% hydrogen peroxide per 2.5 ml of substrate buffer solution, immediately prior to use.
Stop Solution: 3M H2SO4 Merck
Form: Liquid, 1 vial×20 mL; Storage: Store at room temperature.
Use: To stop the reaction, add 50 µL of 3M H2SO4 per well.
Blocking Agent: Casein (Commercial Powder Milk)
Form: Powder, 1 vial×8 g; Storage: Store at 4-8° C.
Use: Dissolve casein in Wash Buffer to obtain a solution of Wash Buffer 3% casein. Stir until all the powder is dissolved. Blocking solution must be preferably used the same day.
Wash Buffer: Wash Buffer Concentrate (30λ)
Form: Liquid, 1 vial×10 mL; Storage: Store at 4-8° C.
Use: Dilute 1 volume of the 10× Wash Buffer concentrate with 9 volumes of deionized water to obtain the Working Wash Buffer 1× (ie. 1 mL may be diluted up to 10 mL).
Plate:
Form: One microplate with selected peptide Coated eight-stripwells for each antigen (A, B, C); Storage: Store at 4-8° C.
Use: To perform the analysis of one problem sample, take one well from each microplate and store the remaining wells.
Protocol
Additional Materials Required: pipettes and timer; microplate reader with a detector that can measure absorbance at 450 nm or color scale; 1 L graduated cylinder; plate washer or wash bottle; polypropylene tubes for standards and sample dilutions, if needed.
Principle of the Assay
This kit is an indirect type ELISA using a horseradish peroxidase detection system. A microtiter plate coated with specific antigens which are recognized by specific human anti-*Leishmania* IgG. The antigens in turn bind to the human IgG. The anti-*Leishmania* IgG is then labeled by a horseradish-peroxidase anti-human IgG reagent. The detection signal is then generated in proportion to the amount of human antibody.
Assay Procedure
Prior to use, allow the kit to warm to room temperature. Remove the number of stripwells according to your design plan.
Sample Dilution Procedure: tested samples and Human Control Serum should be diluted at 1:150 in Blocking Buffer.
Wash the wells 3 times with 100 µL Wash Buffer for 5 minutes before using.

1. Block the wells with 100 µL of Blocking Solution for 2 hours.
2. Discard the Blocking Buffer by tapping.
3. Add 100 µl of the appropriate human serum sample dilution to each well. For the positive control wells, add 100 µl of diluted Human Serum Control serum sample. All serum samples should be diluted in Blocking Buffer. Incubate at room temperature for 2 hours.
4. Remove contents inverting the plate into the sink. Add 200 µL of Working Wash Buffer 1× into each well and remove by inverting the plate into the sink and tap on absorbent paper to remove access liquid. Repeat washes, three times, five minutes each wash.
5. Add 100 µL of diluted Horseradish Peroxidase Anti-Human IgG conjugate solution into each well. Incubate at room temperature for 1 hour.
6. Remove contents inverting the plate into the sink. Repeat washes as in Step 4, three times, five minutes each wash.
7. Add 100 µl of the Developing Solution into each well. Incubate at room temperature for 10-15 min.
8. Quickly add 50 µL of Stop Solution into each well and shake for a few seconds. A dramatic color change from yellow to dark orange should occur.
9. Measure absorbance at 490 nm within 1 hour of adding the Stop Solution.

Verify the assay: The assay can be considered valid if the protocol has been followed correctly; the Positive Control optical density is greater than 0.8 and the ratio of the Cut-off Calibrator to the Negative Control is greater than 2.0.

Interpret the Results:

Score results with an optical density greater than Cut-off 0.3 as positive.

Score results with an optical density less than Cut-off 0.1 as negative.

Results between these values, that is 0.1<Cut-off<0.3, are equivocal and should be repeated to confirm the status.

If the result is uncertain, additional steps are added to the method to increase accuracy and sensitivity:

c) contacting said biological sample with one the peptide H2A-P9 of sequence KGGKKGKATPSA (SEQ. ID. No 9) and d) detecting the presence or absence of the immune complex formed in c).

REFERENCES

1. Braz R F, Nascimento E T, Martins D R, et al. The sensitivity and specificity of *Leishmania chagasi* recombinant K39 antigen in the diagnosis of American visceral leishmaniasis and in differentiating active from subclinical infection. Am J Trop Med Hyg 2002; 67:344-8
2. Reithinger R, Dujardin J C, Louzir H, Pirmez C, Alexander B, Brooker S. Cutaneous leishmaniasis. Lancet Infect Dis. 2007 September; 7(9):581-96. Review. PMID: 17714672
3. Alvar J, Croft S and Olliaro P. Chemotherapy in the treatment and control of leishmaniasis. Adv Parasitol 2006; 61:223-74
4. Boggild A K, Ramos A P, Espinosa D, et al. Clinical and demographic stratification of test performance: a pooled analysis of five laboratory diagnostic methods for American cutaneous leishmaniasis. Am J Trop Med Hyg 2010; 83:345-50
5. Cuba C A C. Diagnostico Parasitologico de la Leishmaniasis Tegumentaria Americana. Revista Peruana de Medicina Experimental y Salud Publica 2000:39-42
6. Luz Z M, Silva A R, Silva Fde O, Caligiorne R B, Oliveira E and Rabello A. Lesion aspirate culture for the diagnosis and isolation of *Leishmania* spp. from patients with cutaneous leishmaniasis. Mem Inst Oswaldo Cruz 2009; 104:62-6
7. Romero G A, Sampaio R N, O. M V and Marsden P D. Sensitivity of a vacuum aspiratory culture technique for diagnosis of localized cutaneous leishmaniasis in an endemic area of *Leishmania* (*Viannia*) *braziliensis* transmission. Mem Inst Oswaldo Cruz 1999; 94:505-8
8. Marzochi M C, Teixeira P C, Marzochi K B, da Conceição N F, Coutinho W and de Brito D B. Vacuum aspiratory puncture system for *Leishmania* culturing, isolation and transport. Preliminary report. Rev Inst Med Trop Sao Paulo 1993; 35:301-3
9. Saki J, Akhlaghi L, Maraghi S, et al. Evaluation of Modified Novy-MacNeal-Nicolle Medium for Isolation of *Leishmania* Parasites from Cutaneous Lesions of Patients in Iran. Res J Parasitol 2009; 4:56-62
10. Aviles H, Belli A, Armijos R, Monroy F P and Harris E. PCR detection and identification of *Leishmania* parasites in clinical specimens in Ecuador: a comparison with classical diagnostic methods. J Parasitol 1999; 85:181-7
11. Barroso-Freitas A P, Passos S R, Mouta-Confort E, et al. Accuracy of an ELISA and indirect mmunofluorescence for the laboratory diagnosis of American tegumentary leishmaniasis. Trans R Soc Trop Med Hyg 2009; 103: 383-9
12. Junqueira Pedras M, Orsini M, Castro M, Passos V M and Rabello A. Antibody subclass profile against *Leishmania braziliensis* and *Leishmania amazonensis* in the diagnosis and follow-up of mucosal leishmaniasis. Diagn Microbiol Infect Dis 2003; 47:477-85
13. Ryan J R, Smithyman A M, Rajasekariah G, Hochberg L, Stiteler J M and Martin S K. Enzyme-Linked Immunosorbent Assay Based on Soluble Promastigote Antigen Detects Immunoglobulin M (IgM) and IgG Antibodies in Sera from Cases of Visceral and Cutaneous Leishmaniasis J Clin Microbiol 2002; 40:1037-43
14. Guimaraes M C, Celeste B J and Franco E L. Diagnostic performance indices for immunofluorescent tests and enzyme immunoassays of leishmaniasis sera from northern and north-eastern Brazil. Bull World Health Organ 1990; 68:39-43
15. Guimaraes M C, Celeste B J, Franco E L, Cucé L C and Belda W J. Evaluation of serological diagnostic indices for mucocutaneous leishmaniasis: immunofluorescence tests and enzyme-linked immunoassays for IgG, IgM and IgA antibodies. Bull World Health Organ 1989; 67:643-8
16. Carmelo E, Martinez E, Gonzales A C, et al. Antigenicity of *Leishmania braziliensis* Histone H1 during Cutaneous Leishmaniasis: Localization of Antigenic Determinants Clin Diagn Lab Immunol 2002; 9:808-11
17. Webb J R, Campos-Neto A, Ovendale P J, et al. Human and murine immune responses to a novel *Leishmania major* recombinant protein encoded by members of a multicopy gene family. Infect Immun 1998; 66:3279-89
18. Montoya Y, Leon C, Talledo M, et al. Recombinant antigens for specific and sensitive serodiagnosis of Latin American tegumentary leishmaniasis Trans R Soc Trop Med Hyg 1997; 91:674-6
19. Celeste B J, Angel S O, Castro L G, Gidlund M and Goto H. *Leishmania infantum* heat shock protein 83 for the serodiagnosis of tegumentary leishmaniasis. Braz J Med Biol Res 2004; 37:1591-3
20. Amorim A, Carrington M, Miles M A, Barker D C and de Almeida L C. Identification of the C-terminal region of 20. 70 kDa heat shock protein from *Leishmania* (*Viannia*) *braziliensis* as a target for the humoral immune response. Cell Stress Chaperones 1996; 1:177-87
21. Myler H A, McVay S, Kratzsch J. Troubleshooting PEG-hGH detection supporting pharmacokinetic evaluation in growth hormone deficient patients. J Pharmacol Toxicol Methods. 2010 March April; 61(2):92-7. Epub 2010 Jan. 4.
22. Noya O, Patarroyo M E, Guzmán F and B. AdN. Immunodiagnosis of Parasitic Diseases with Synthetic Peptides. Current Protein and Peptide Science 2003; 4:299-308
23. Gomara M J, Haro I. Synthetic peptides for the immunodiagnosis of human diseases. Curr Med Chem 2007; 14:531-46
24. Soto M, Requena J M, Quijada L, et al. Antigenicity of the *Leishmania infantum* histones H2B and H4 during canine viscerocutaneous leishmaniasis. Clin Exp Immunol 1999; 115:342-9
25. Soto M, Requena J, Quijada L, et al. During active viscerocutaneous leishmaniasis the anti-P2 humoral response is specifically triggered by the parasite P proteins. Clinical and Experimental Immunology 1995; 100: 246-52
26. Soto M, Requena J M, Quijada L, et al. Mapping of the linear antigenic determinants from the *Leishmania infantum* histone H2A recognized by sera from dogs with leishmaniasis. Immunol Lett 1995; 48:209-14
27. Soto M, Requena J M, Quijada L, et al. Characterization of the antigenic determinants of the *Leishmania infantum* histone H3 recognized by antibodies elicited during canine visceral leishmaniasis. Clin Exp Immunol 1996; 106:454-61
28. Soto M, Requena J M, Quijada L, Guzman F, Patarroyo M E and Alonso C. Identification of the *Leishmania infantum* P0 ribosomal protein epitope in canine visceral leishmaniasis. Immunol Lett 1995; 48:23-8
29. Soto M, Requena J M, Quijada L and Alonso C. Specific serodiagnosis of human leishmaniasis with recombinant *Leishmania* P2 acidic ribosomal proteins. Clin Diagn Lab Immunol 1996; 3:387-91
30. Gonzalez A C, Martinez E, Carmelo E, et al. Analysis of NLS and rRNA binding motifs in the L25 ribosomal protein from *Leishmania* (*viannia*) *braziliensis*: investigation of its diagnostic capabilities. Parasitology 2002; 125:51-7
31. Coleman A S, Rossmann E, Yang X, et al. BBK07 immunodominant peptides as serodiagnostic markers of Lyme disease. Clin Vaccine Immunol 2011; 18:406-13
32. Pau C P, Lam L L, Spira T J, et al. Mapping and serodiagnostic application of a dominant epitope within the human herpesvirus 8 ORF 65-encoded protein. J Clin Microbiol 1998; 36:1574-7
33. Singh K K, Sharma N, Vargas D, et al. Peptides of a novel *Mycobacterium tuberculosis* specific cell wall protein for immunodiagnosis of tuberculosis. J Infect Dis 2009; 200:571-81
34. Soto M, Requena J M, Gomez L C, Navarrete I and Alonso C. Molecular characterization of a *Leishmania donovani infantum* antigen identified as histone H2A. Eur J Biochem 1992; 205:211-6
35. Soto M, Requena J M, Morales G and Alonso C. The *Leishmania infantum* histone H3 possesses an extremely divergent N-terminal domain Biochim Biophys Acta 1994; 1219:533-5
36. Soto M, Quijada L, Alonso C and Requena J M. Molecular cloning and analysis of expression of the *Leishmania infantum* histone H4 genes. Mol Biochem Parasitol 1997; 90:439-47
37. Iborra S, Soto M, Carrion J, et al. The *Leishmania infantum* acidic ribosomal protein P0 administered as a DNA vaccine confers protective immunity to *Leishmania major* infection in BALB/c mice. Infect Immun 2003; 71:6562-72
38. Soto M, Requena J M and Alonso C. Isolation, characterization and analysis of the expression of the *Leishmania* ribosomal P0 protein genes. Mol Biochem Parasitol 1993; 61:265-74
39. Soto M, Requena J M, Garcia M, Gomez L C, Navarrete I and Alonso C. Genomic organization and expression of two independent gene arrays coding for two antigenic acidic ribosomal proteins of *Leishmania*. J Biol Chem 1993; 268:21835-43
40. Soto M, Requena J, Quijada L and Alonso C. Multicomponent Chimeric Antigen for Serodiagnosis of Canine Visceral Leishmaniasis. Journal of Clinical Microbiology 1998; 36:58-63
41. Houghten R A. General method for the rapid solid-phase synthesis of large numbers of peptides: specificity of antigen-antibody interaction at the level of individual amino acids. Proc Natl Acad Sci USA 1985; 82:5131-5
42. Zagui D, Panosian C, Gutierrez M A, Gregson A, Taylor E and Ochoa M T. New World cutaneous leishmaniasis: current challenges in diagnosis and parenteral treatment. J Am Acad Dermatol 2011; 64:587-92
43. Boggild A K, Miranda-Verastegui C, Espinosa D, et al. Evaluation of a microculture method for isolation of *Leishmania* parasites from cutaneous lesions of patients in Peru. J Clin Microbiol 2007; 45:3680-4
44. Boggild A K, Ramos A P, Valencia B M, et al. Diagnostic performance of filter paper lesion impression PCR for secondarily infected ulcers and nonulcerative lesions caused by cutaneous leishmaniasis J Clin Microbiol 2011; 49:1097-100
45. Pirmez C, da Silva Trajano V, Paes-Oliveira Neto M, et al. Use of PCR in diagnosis of human american tegumentary leishmaniasis in Rio de Janeiro, Brazil. J Clin Microbiol 1999; 37:1819-23
46. Brito M E, Mendonca M G, Gomes Y M, Jardim M L and Abath F G. Identification of Potentially Diagnostic *Leishmania braziliensis* Antigens in Human Cutaneous Leishmaniasis by Immunoblot Analysis. Clin Diagn Lab Immunol 2000; 7:318-21
47. Goncalves C C, Reiche E M, De Abreu Filho B A, et al. Evaluation of antigens from various *Leishmania* species in a Western blot for diagnosis of American tegumentary leishmaniasis. Am J Trop Med Hyg 2002; 66:91-102
48. Goto H, Lauletta Lindoso J A. Current diagnosis and treatment of cutaneous and mucocutaneous leishmaniasis. Expert Reviews of Anti-infective Therapy 2010; 8:419-33
49. Maalej I A, Chenik M, Louzir H, et al. Comparative evaluation of ELISAs based on ten recombinant or purified *Leishmania* antigens for the serodiagnosis of Mediterranean Visceral Leishmaniasis. Am J Trop Med Hyg 2003; 68:312-20
50. Levin M J, Vazquez M, Kaplan D and Schijman A G. The *Trypanosoma cruzi* Ribosomal P Protein Family: Classification and Antigenicity. Parasitol Today 1993; 9:381-4

SEQUENCES LISTING

| | | |
|---|---|---|
| SEQ. ID. No 1 | H2A P1 | MATPRSAKKAVRKSGSKSAK |
| SEQ. ID. No 2 | H2A P2 | SKSAKCGLIFPVGRVGGMMR |
| SEQ. ID. No 3 | H2A P3 | GGMM RRGQYARRIGASGAVY |
| SEQ. ID. No 4 | H2A P4 | SGAVYLAAVLEYLTAELLEL |
| SEQ. ID. No 5 | H2A P5 | ELLELSVKAAAQSGKKRCRL |
| SEQ. ID. No 6 | H2A P6 | KRCRLNPRTVMLAARHDDDI |
| SEQ. ID. No 7 | H2A P7 | HDDDIGTLLKNVTLSHSGVV |
| SEQ. ID. No 8 | H2A P8 | HSGVVPNISKAMAKKKGGKK |
| SEQ. ID. No 9 | H2A P9 | KGGKKGKATPSA |
| SEQ. ID. No 10 | H2B P1 | MASSRSAPRKASHAHKSHRK |
| SEQ. ID. No 11 | H2B P2 | ASHAHKSHRKPKRSWNVYVG |
| SEQ. ID. No 12 | H2B P3 | PKRSWNVYVGRSLKAINAQM |
| SEQ. ID. No 13 | H2B P4 | RSLKAINAQMSMSHRTMSIV |
| SEQ. ID. No 14 | H2B P5 | SMSHRTMSIVNSYVNDVMER |
| SEQ. ID. No 15 | H2B P6 | NSYVNDVMERICMEAASIVR |
| SEQ. ID. No 16 | H2B P7 | ICMEAASIVRANKKRTLGAR |
| SEQ. ID. No 17 | H2B P8 | ANKKRTLGAREVQTAVRIVL |
| SEQ. ID. No 18 | H2B P9 | EVQTAVRIVLPAELAKHAMA |
| SEQ. ID. No 19 | H2B P10 | PAELAKHAMAEGTKAVSSASA |
| SEQ. ID. No 20 | H3 P1 | MSRTKETARAKRTITSKKSK |
| SEQ. ID. No 21 | H3 P2 | KRTITSKKSKKAPSGASGVK |
| SEQ. ID. No 22 | H3 P3 | KAPSGASGVKRSHRRWRPGT |
| SEQ. ID. No 23 | H3 P4 | RSHRRWRPGTCAIREIRKFQ |
| SEQ. ID. No 24 | H3 P5 | CAIREIRKFQKSTSLLIQCA |
| SEQ. ID. No 25 | H3 P6 | KSTSLLIQCAPFQRLVRGVE |
| SEQ. ID. No 26 | H3 P7 | PFQRLVRGVERQKEGLRFQS |
| SEQ. ID. No 27 | H3 P8 | RQKEGLRFQSSAIMALQEAT |
| SEQ. ID. No 28 | H3 P9 | SAIMALQEATEAYIVSLMAD |
| SEQ. ID. No 29 | H3 P10 | EAYIVSLMADTNLACIHAKR |
| SEQ. ID. No 30 | H3 P11 | TNLACIHAKRVTIQPKDIQL |
| SEQ. ID. No 31 | H3 P12 | VTIQPKDIQLALRLRGERH |
| SEQ. ID. No 32 | H4 P1 | MAKGKRSTDAKGSQRRQKKV |
| SEQ. ID. No 33 | H4 P2 | KGSQRRQKKVLRDNIRGITR |
| SEQ. ID. No 34 | H4 P3 | LRDNIRGITRGCVRRMARRG |
| SEQ. ID. No 35 | H4 P4 | GCVRRMARRGGVKRISTEVY |
| SEQ. ID. No 36 | H4 P5 | GVKRISTEVYEEVRRVLKAY |
| SEQ. ID. No 37 | H4 P6 | EEVRRVLKAYVEDIVRCSTA |
| SEQ. ID. No 38 | H4 P7 | VEDIVRCSTAYTEYARKKTV |
| SEQ. ID. No 39 | H4 P8 | YTEYARKKTVTACDVVTALR |
| SEQ. ID. No 40 | H4 P9 | TACDVVTALRKQGHILYGYA |
| SEQ. ID. No 41 | P0 P1 | MPSITTAKREYEERLVDCLT |
| SEQ. ID. No 42 | P0 P2 | VDCLTKYSCVLFVGMDNVRS |
| SEQ. ID. No 43 | P0 P3 | DNVRSQQVHDVGRALRAKAE |
| SEQ. ID. No 44 | P0 P4 | RAKAEFMMGKKTLQGKIVEK |
| SEQ. ID. No 45 | P0 P5 | KIVEKRAQAKDASPEAKHFN |
| SEQ. ID. No 46 | P0 P6 | AKHFNDQCEEYNLVTRNTGL |
| SEQ. ID. No 47 | P0 P7 | RNTGLIFTNNAVQEITSVLD |
| SEQ. ID. No 48 | P0 P8 | TSVLDAHRVKRAARVGAISP |
| SEQ. ID. No 49 | P0 P9 | GAISPCDVIVAAGSTGMEPT |
| SEQ. ID. No 50 | P0 P10 | GMEPTQTSFFQALMIATKIA |
| SEQ. ID. No 51 | P0 P11 | ATKIAKGMVEIVTEKKVLSV |
| SEQ. ID. No 52 | P0 P12 | LLQKLNISPFYYQVNVLSVW |
| SEQ. ID. No 53 | P0 P13 | VLSVWDRGDLFTREDLMMTE |
| SEQ. ID. No 54 | P0 P14 | LMMTEDMVEKMLMEGLSNVA |
| SEQ. ID. No 55 | P0 P15 | LSNVAAMALGAGIPTSSTIG |
| SEQ. ID. No 56 | P0 P16 | SSTIGPMLVDAFKNLLAVSV |
| SEQ. ID. No 57 | P0 P17 | LAVSVATSYEFEEHNGKELR |
| SEQ. ID. No 58 | P0 P18 | GKELREAAIMGLLAGSCSAA |
| SEQ. ID. No 59 | P0 P19 | SCSAAAEPAAAAPAAPSAAA |
| SEQ. ID. No 60 | P0 P20 | PSAAAKEEPEESDEDDFGMG |
| SEQ. ID. No 61 | P0 P21 | AAKEEPEESDEDDFGMGGLF |
| SEQ. ID. No 62 | P2a P1 | MQYLAAYALVALSGKTPSKA |
| SEQ. ID. No 63 | P2a P2 | TPSKADVQAVLKAAGVAVDA |
| SEQ. ID. No 64 | P2a P3 | VAVDASRVDAVFQEVEGKSF |
| SEQ. ID. No 65 | P2a P4 | EGKSFDALVAEGRTKLVGSG |
| SEQ. ID. No 66 | P2a P5 | LVGSGSAAPAGAVSTAGAGA |
| SEQ. ID. No 67 | P2a P6 | AGAGAGAVAEAKKEEPEEE |
| SEQ. ID. No 68 | P2a P7 | PEEEEADDDMGFGLFD |
| SEQ. ID. No 69 | P2b P1 | MSTKYLAAYALASLSKASPS |
| SEQ. ID. No 70 | P2b P2 | KASPSQADVEAICKAVHIDV |
| SEQ. ID. No 71 | P2b P3 | VHIDVDQATLAFVMESVTGR |
| SEQ. ID. No 72 | P2b P4 | SVTGRDVATLIAEGAAKMSA |
| SEQ. ID. No 73 | P2b P5 | AKMSAMPAASSGAAAGVTAS |
| SEQ. ID. No 74 | P2b P6 | GVTASAAGDAAPAAAAKKD |
| SEQ. ID. No 75 | P2b P7 | AAKKDEPEEEADDDMGFGLFD |

The invention claimed is:

1. In vitro diagnostic method for the detection of the presence or absence of antibodies indicative of a South American *Leishmania* strain responsible for the American Tegumentary Leishmaniasis, comprising the steps of:

a) contacting H2A-P9 (SEQ. ID. NO. 9) and P2a-P6 (SEQ. ID. NO. 67) with a biological sample for a time and under conditions sufficient to form a first immune complex comprising a first antibody bound to SEQ. ID. NO. 9 and a second immune complex comprising a second antibody bound to SEQ. ID. NO. 67; and b) detecting the presence or absence of the first immune complex and second immune complex formed in a)

wherein detecting the presence of the first immune complex and the second immune complex indicates the presence of antibodies indicative of a South American *Leishmania* strain.

2. In vitro diagnostic method according to claim 1, wherein said South American *Leishmania* strain is selected in the group consisting of *L. braziliensis, L. mexicana, L. major, L. amazonensis* or *L. infantum.*

3. In vitro diagnostic method according to claim 1, wherein said method comprises two additional steps c) and d) consisting in:

c) contacting said biological sample with the peptide H2A-P9 of sequence KGGKKGKATPSA (SEQ. ID. NO. 9) for a time and under conditions sufficient to form a third immune complex comprising SEQ. ID. NO. 9 and a third antibody; and d) detecting the presence or absence of the immune complex formed in c), wherein detecting the presence of the third immune complex indicates the presence of antibodies indicative of a South American *Leishmania* strain.

* * * * *

SEQUENCE LISTING

<160> NUMBER OF SEQ ID NOS: 75

<210> SEQ ID NO 1
<211> LENGTH: 20
<212> TYPE: PRT
<213> ORGANISM: Leishmania infantum

<400> SEQUENCE: 1

Met Ala Thr Pro Arg Ser Ala Lys Lys Ala Val Arg Lys Ser Gly Ser
1               5                   10                  15

Lys Ser Ala Lys
            20

<210> SEQ ID NO 2
<211> LENGTH: 20
<212> TYPE: PRT
<213> ORGANISM: Leishmania infantum

<400> SEQUENCE: 2

Ser Lys Ser Ala Lys Cys Gly Leu Ile Phe Pro Val Gly Arg Val Gly
1               5                   10                  15

Gly Met Met Arg
            20

<210> SEQ ID NO 3
<211> LENGTH: 20
<212> TYPE: PRT
<213> ORGANISM: Leishmania infantum

<400> SEQUENCE: 3

Gly Gly Met Met Arg Arg Gly Gln Tyr Ala Arg Arg Ile Gly Ala Ser
1               5                   10                  15

Gly Ala Val Tyr
            20

<210> SEQ ID NO 4
<211> LENGTH: 20
<212> TYPE: PRT
<213> ORGANISM: Leishmania infantum

<400> SEQUENCE: 4

Ser Gly Ala Val Tyr Leu Ala Ala Val Leu Glu Tyr Leu Thr Ala Glu
1               5                   10                  15

Leu Leu Glu Leu
            20

<210> SEQ ID NO 5
<211> LENGTH: 20
<212> TYPE: PRT
<213> ORGANISM: Leishmania infantum

<400> SEQUENCE: 5

Glu Leu Leu Glu Leu Ser Val Lys Ala Ala Ala Gln Ser Gly Lys Lys
1               5                   10                  15

Arg Cys Arg Leu
            20

<210> SEQ ID NO 6
<211> LENGTH: 20
<212> TYPE: PRT
<213> ORGANISM: Leishmania infantum

<400> SEQUENCE: 6

```
Lys Arg Cys Arg Leu Asn Pro Arg Thr Val Met Leu Ala Ala Arg His
1               5                   10                  15

Asp Asp Asp Ile
            20

<210> SEQ ID NO 7
<211> LENGTH: 20
<212> TYPE: PRT
<213> ORGANISM: Leishmania infantum

<400> SEQUENCE: 7

His Asp Asp Asp Ile Gly Thr Leu Leu Lys Asn Val Thr Leu Ser His
1               5                   10                  15

Ser Gly Val Val
            20

<210> SEQ ID NO 8
<211> LENGTH: 20
<212> TYPE: PRT
<213> ORGANISM: Leishmania infantum

<400> SEQUENCE: 8

His Ser Gly Val Val Pro Asn Ile Ser Lys Ala Met Ala Lys Lys Lys
1               5                   10                  15

Gly Gly Lys Lys
            20

<210> SEQ ID NO 9
<211> LENGTH: 12
<212> TYPE: PRT
<213> ORGANISM: Leishmania infantum

<400> SEQUENCE: 9

Lys Gly Gly Lys Lys Gly Lys Ala Thr Pro Ser Ala
1               5                   10

<210> SEQ ID NO 10
<211> LENGTH: 20
<212> TYPE: PRT
<213> ORGANISM: Leishmania infantum

<400> SEQUENCE: 10

Met Ala Ser Ser Arg Ser Ala Pro Arg Lys Ala Ser His Ala His Lys
1               5                   10                  15

Ser His Arg Lys
            20

<210> SEQ ID NO 11
<211> LENGTH: 20
<212> TYPE: PRT
<213> ORGANISM: Leishmania infantum

<400> SEQUENCE: 11

Ala Ser His Ala His Lys Ser His Arg Lys Pro Lys Arg Ser Trp Asn
1               5                   10                  15

Val Tyr Val Gly
            20

<210> SEQ ID NO 12
<211> LENGTH: 20
<212> TYPE: PRT
<213> ORGANISM: Leishmania infantum
```

```
<400> SEQUENCE: 12

Pro Lys Arg Ser Trp Asn Val Tyr Val Gly Arg Ser Leu Lys Ala Ile
1               5                   10                  15

Asn Ala Gln Met
            20

<210> SEQ ID NO 13
<211> LENGTH: 20
<212> TYPE: PRT
<213> ORGANISM: Leishmania infantum

<400> SEQUENCE: 13

Arg Ser Leu Lys Ala Ile Asn Ala Gln Met Ser Met Ser His Arg Thr
1               5                   10                  15

Met Ser Ile Val
            20

<210> SEQ ID NO 14
<211> LENGTH: 20
<212> TYPE: PRT
<213> ORGANISM: Leishmania infantum

<400> SEQUENCE: 14

Ser Met Ser His Arg Thr Met Ser Ile Val Asn Ser Tyr Val Asn Asp
1               5                   10                  15

Val Met Glu Arg
            20

<210> SEQ ID NO 15
<211> LENGTH: 20
<212> TYPE: PRT
<213> ORGANISM: Leishmania infantum

<400> SEQUENCE: 15

Asn Ser Tyr Val Asn Asp Val Met Glu Arg Ile Cys Met Glu Ala Ala
1               5                   10                  15

Ser Ile Val Arg
            20

<210> SEQ ID NO 16
<211> LENGTH: 20
<212> TYPE: PRT
<213> ORGANISM: Leishmania infantum

<400> SEQUENCE: 16

Ile Cys Met Glu Ala Ala Ser Ile Val Arg Ala Asn Lys Lys Arg Thr
1               5                   10                  15

Leu Gly Ala Arg
            20

<210> SEQ ID NO 17
<211> LENGTH: 20
<212> TYPE: PRT
<213> ORGANISM: Leishmania infantum

<400> SEQUENCE: 17

Ala Asn Lys Lys Arg Thr Leu Gly Ala Arg Glu Val Gln Thr Ala Val
1               5                   10                  15

Arg Ile Val Leu
            20
```

<210> SEQ ID NO 18
<211> LENGTH: 20
<212> TYPE: PRT
<213> ORGANISM: Leishmania infantum

<400> SEQUENCE: 18

Glu Val Gln Thr Ala Val Arg Ile Val Leu Pro Ala Glu Leu Ala Lys
1               5                   10                  15

His Ala Met Ala
            20

<210> SEQ ID NO 19
<211> LENGTH: 21
<212> TYPE: PRT
<213> ORGANISM: Leishmania infantum

<400> SEQUENCE: 19

Pro Ala Glu Leu Ala Lys His Ala Met Ala Glu Gly Thr Lys Ala Val
1               5                   10                  15

Ser Ser Ala Ser Ala
            20

<210> SEQ ID NO 20
<211> LENGTH: 20
<212> TYPE: PRT
<213> ORGANISM: Leishmania infantum

<400> SEQUENCE: 20

Met Ser Arg Thr Lys Glu Thr Ala Arg Ala Lys Arg Thr Ile Thr Ser
1               5                   10                  15

Lys Lys Ser Lys
            20

<210> SEQ ID NO 21
<211> LENGTH: 20
<212> TYPE: PRT
<213> ORGANISM: Leishmania infantum

<400> SEQUENCE: 21

Lys Arg Thr Ile Thr Ser Lys Lys Ser Lys Lys Ala Pro Ser Gly Ala
1               5                   10                  15

Ser Gly Val Lys
            20

<210> SEQ ID NO 22
<211> LENGTH: 20
<212> TYPE: PRT
<213> ORGANISM: Leishmania infantum

<400> SEQUENCE: 22

Lys Ala Pro Ser Gly Ala Ser Gly Val Lys Arg Ser His Arg Arg Trp
1               5                   10                  15

Arg Pro Gly Thr
            20

<210> SEQ ID NO 23
<211> LENGTH: 20
<212> TYPE: PRT
<213> ORGANISM: Leishmania infantum

<400> SEQUENCE: 23

Arg Ser His Arg Arg Trp Arg Pro Gly Thr Cys Ala Ile Arg Glu Ile

```
1               5                   10                  15

Arg Lys Phe Gln
            20

<210> SEQ ID NO 24
<211> LENGTH: 20
<212> TYPE: PRT
<213> ORGANISM: Leishmania infantum

<400> SEQUENCE: 24

Cys Ala Ile Arg Glu Ile Arg Lys Phe Gln Lys Ser Thr Ser Leu Leu
1               5                   10                  15

Ile Gln Cys Ala
            20

<210> SEQ ID NO 25
<211> LENGTH: 20
<212> TYPE: PRT
<213> ORGANISM: Leishmania infantum

<400> SEQUENCE: 25

Lys Ser Thr Ser Leu Leu Ile Gln Cys Ala Pro Phe Gln Arg Leu Val
1               5                   10                  15

Arg Gly Val Glu
            20

<210> SEQ ID NO 26
<211> LENGTH: 20
<212> TYPE: PRT
<213> ORGANISM: Leishmania infantum

<400> SEQUENCE: 26

Pro Phe Gln Arg Leu Val Arg Gly Val Glu Arg Gln Lys Glu Gly Leu
1               5                   10                  15

Arg Phe Gln Ser
            20

<210> SEQ ID NO 27
<211> LENGTH: 20
<212> TYPE: PRT
<213> ORGANISM: Leishmania infantum

<400> SEQUENCE: 27

Arg Gln Lys Glu Gly Leu Arg Phe Gln Ser Ser Ala Ile Met Ala Leu
1               5                   10                  15

Gln Glu Ala Thr
            20

<210> SEQ ID NO 28
<211> LENGTH: 20
<212> TYPE: PRT
<213> ORGANISM: Leishmania infantum

<400> SEQUENCE: 28

Ser Ala Ile Met Ala Leu Gln Glu Ala Thr Glu Ala Tyr Ile Val Ser
1               5                   10                  15

Leu Met Ala Asp
            20

<210> SEQ ID NO 29
<211> LENGTH: 20
<212> TYPE: PRT
```

<213> ORGANISM: Leishmania infantum

<400> SEQUENCE: 29

Glu Ala Tyr Ile Val Ser Leu Met Ala Asp Thr Asn Leu Ala Cys Ile
1               5                   10                  15

His Ala Lys Arg
            20

<210> SEQ ID NO 30
<211> LENGTH: 20
<212> TYPE: PRT
<213> ORGANISM: Leishmania infantum

<400> SEQUENCE: 30

Thr Asn Leu Ala Cys Ile His Ala Lys Arg Val Thr Ile Gln Pro Lys
1               5                   10                  15

Asp Ile Gln Leu
            20

<210> SEQ ID NO 31
<211> LENGTH: 19
<212> TYPE: PRT
<213> ORGANISM: Leishmania infantum

<400> SEQUENCE: 31

Val Thr Ile Gln Pro Lys Asp Ile Gln Leu Ala Leu Arg Leu Arg Gly
1               5                   10                  15

Glu Arg His

<210> SEQ ID NO 32
<211> LENGTH: 20
<212> TYPE: PRT
<213> ORGANISM: Leishmania infantum

<400> SEQUENCE: 32

Met Ala Lys Gly Lys Arg Ser Thr Asp Ala Lys Gly Ser Gln Arg Arg
1               5                   10                  15

Gln Lys Lys Val
            20

<210> SEQ ID NO 33
<211> LENGTH: 20
<212> TYPE: PRT
<213> ORGANISM: Leishmania infantum

<400> SEQUENCE: 33

Lys Gly Ser Gln Arg Arg Gln Lys Lys Val Leu Arg Asp Asn Ile Arg
1               5                   10                  15

Gly Ile Thr Arg
            20

<210> SEQ ID NO 34
<211> LENGTH: 20
<212> TYPE: PRT
<213> ORGANISM: Leishmania infantum

<400> SEQUENCE: 34

Leu Arg Asp Asn Ile Arg Gly Ile Thr Arg Gly Cys Val Arg Arg Met
1               5                   10                  15

Ala Arg Arg Gly
            20

<210> SEQ ID NO 35
<211> LENGTH: 20
<212> TYPE: PRT
<213> ORGANISM: Leishmania infantum

<400> SEQUENCE: 35

Gly Cys Val Arg Arg Met Ala Arg Arg Gly Gly Val Lys Arg Ile Ser
1               5                   10                  15

Thr Glu Val Tyr
            20

<210> SEQ ID NO 36
<211> LENGTH: 20
<212> TYPE: PRT
<213> ORGANISM: Leishmania infantum

<400> SEQUENCE: 36

Gly Val Lys Arg Ile Ser Thr Glu Val Tyr Glu Val Arg Arg Val
1               5                   10                  15

Leu Lys Ala Tyr
            20

<210> SEQ ID NO 37
<211> LENGTH: 20
<212> TYPE: PRT
<213> ORGANISM: Leishmania infantum

<400> SEQUENCE: 37

Glu Glu Val Arg Arg Val Leu Lys Ala Tyr Val Glu Asp Ile Val Arg
1               5                   10                  15

Cys Ser Thr Ala
            20

<210> SEQ ID NO 38
<211> LENGTH: 20
<212> TYPE: PRT
<213> ORGANISM: Leishmania infantum

<400> SEQUENCE: 38

Val Glu Asp Ile Val Arg Cys Ser Thr Ala Tyr Thr Glu Tyr Ala Arg
1               5                   10                  15

Lys Lys Thr Val
            20

<210> SEQ ID NO 39
<211> LENGTH: 20
<212> TYPE: PRT
<213> ORGANISM: Leishmania infantum

<400> SEQUENCE: 39

Tyr Thr Glu Tyr Ala Arg Lys Lys Thr Val Thr Ala Cys Asp Val Val
1               5                   10                  15

Thr Ala Leu Arg
            20

<210> SEQ ID NO 40
<211> LENGTH: 20
<212> TYPE: PRT
<213> ORGANISM: Leishmania infantum

<400> SEQUENCE: 40

Thr Ala Cys Asp Val Val Thr Ala Leu Arg Lys Gln Gly His Ile Leu

-continued

```
1               5                   10                  15

Tyr Gly Tyr Ala
            20

<210> SEQ ID NO 41
<211> LENGTH: 20
<212> TYPE: PRT
<213> ORGANISM: Leishmania infantum

<400> SEQUENCE: 41

Met Pro Ser Ile Thr Thr Ala Lys Arg Glu Tyr Glu Glu Arg Leu Val
1               5                   10                  15

Asp Cys Leu Thr
            20

<210> SEQ ID NO 42
<211> LENGTH: 20
<212> TYPE: PRT
<213> ORGANISM: Leishmania infantum

<400> SEQUENCE: 42

Val Asp Cys Leu Thr Lys Tyr Ser Cys Val Leu Phe Val Gly Met Asp
1               5                   10                  15

Asn Val Arg Ser
            20

<210> SEQ ID NO 43
<211> LENGTH: 20
<212> TYPE: PRT
<213> ORGANISM: Leishmania infantum

<400> SEQUENCE: 43

Asp Asn Val Arg Ser Gln Gln Val His Asp Val Gly Arg Ala Leu Arg
1               5                   10                  15

Ala Lys Ala Glu
            20

<210> SEQ ID NO 44
<211> LENGTH: 20
<212> TYPE: PRT
<213> ORGANISM: Leishmania infantum

<400> SEQUENCE: 44

Arg Ala Lys Ala Glu Phe Met Met Gly Lys Lys Thr Leu Gln Gly Lys
1               5                   10                  15

Ile Val Glu Lys
            20

<210> SEQ ID NO 45
<211> LENGTH: 20
<212> TYPE: PRT
<213> ORGANISM: Leishmania infantum

<400> SEQUENCE: 45

Lys Ile Val Glu Lys Arg Ala Gln Ala Lys Asp Ala Ser Pro Glu Ala
1               5                   10                  15

Lys His Phe Asn
            20

<210> SEQ ID NO 46
<211> LENGTH: 20
<212> TYPE: PRT
```

```
<213> ORGANISM: Leishmania infantum

<400> SEQUENCE: 46

Ala Lys His Phe Asn Asp Gln Cys Glu Glu Tyr Asn Leu Val Thr Arg
1               5                   10                  15

Asn Thr Gly Leu
            20

<210> SEQ ID NO 47
<211> LENGTH: 20
<212> TYPE: PRT
<213> ORGANISM: Leishmania infantum

<400> SEQUENCE: 47

Arg Asn Thr Gly Leu Ile Phe Thr Asn Asn Ala Val Gln Glu Ile Thr
1               5                   10                  15

Ser Val Leu Asp
            20

<210> SEQ ID NO 48
<211> LENGTH: 20
<212> TYPE: PRT
<213> ORGANISM: Leishmania infantum

<400> SEQUENCE: 48

Thr Ser Val Leu Asp Ala His Arg Val Lys Arg Ala Ala Arg Val Gly
1               5                   10                  15

Ala Ile Ser Pro
            20

<210> SEQ ID NO 49
<211> LENGTH: 20
<212> TYPE: PRT
<213> ORGANISM: Leishmania infantum

<400> SEQUENCE: 49

Gly Ala Ile Ser Pro Cys Asp Val Ile Val Ala Ala Gly Ser Thr Gly
1               5                   10                  15

Met Glu Pro Thr
            20

<210> SEQ ID NO 50
<211> LENGTH: 20
<212> TYPE: PRT
<213> ORGANISM: Leishmania infantum

<400> SEQUENCE: 50

Gly Met Glu Pro Thr Gln Thr Ser Phe Phe Gln Ala Leu Met Ile Ala
1               5                   10                  15

Thr Lys Ile Ala
            20

<210> SEQ ID NO 51
<211> LENGTH: 20
<212> TYPE: PRT
<213> ORGANISM: Leishmania infantum

<400> SEQUENCE: 51

Ala Thr Lys Ile Ala Lys Gly Met Val Glu Ile Val Thr Glu Lys Lys
1               5                   10                  15

Val Leu Ser Val
            20
```

-continued

<210> SEQ ID NO 52
<211> LENGTH: 20
<212> TYPE: PRT
<213> ORGANISM: Leishmania infantum

<400> SEQUENCE: 52

Leu Leu Gln Lys Leu Asn Ile Ser Pro Phe Tyr Tyr Gln Val Asn Val
1               5                   10                  15

Leu Ser Val Trp
            20

<210> SEQ ID NO 53
<211> LENGTH: 20
<212> TYPE: PRT
<213> ORGANISM: Leishmania infantum

<400> SEQUENCE: 53

Val Leu Ser Val Trp Asp Arg Gly Asp Leu Phe Thr Arg Glu Asp Leu
1               5                   10                  15

Met Met Thr Glu
            20

<210> SEQ ID NO 54
<211> LENGTH: 20
<212> TYPE: PRT
<213> ORGANISM: Leishmania infantum

<400> SEQUENCE: 54

Leu Met Met Thr Glu Asp Met Val Glu Lys Met Leu Met Glu Gly Leu
1               5                   10                  15

Ser Asn Val Ala
            20

<210> SEQ ID NO 55
<211> LENGTH: 20
<212> TYPE: PRT
<213> ORGANISM: Leishmania infantum

<400> SEQUENCE: 55

Leu Ser Asn Val Ala Ala Met Ala Leu Gly Ala Gly Ile Pro Thr Ser
1               5                   10                  15

Ser Thr Ile Gly
            20

<210> SEQ ID NO 56
<211> LENGTH: 20
<212> TYPE: PRT
<213> ORGANISM: Leishmania infantum

<400> SEQUENCE: 56

Ser Ser Thr Ile Gly Pro Met Leu Val Asp Ala Phe Lys Asn Leu Leu
1               5                   10                  15

Ala Val Ser Val
            20

<210> SEQ ID NO 57
<211> LENGTH: 20
<212> TYPE: PRT
<213> ORGANISM: Leishmania infantum

<400> SEQUENCE: 57

```
Leu Ala Val Ser Val Ala Thr Ser Tyr Glu Phe Glu Glu His Asn Gly
1               5                   10                  15

Lys Glu Leu Arg
            20

<210> SEQ ID NO 58
<211> LENGTH: 20
<212> TYPE: PRT
<213> ORGANISM: Leishmania infantum

<400> SEQUENCE: 58

Gly Lys Glu Leu Arg Glu Ala Ala Ile Met Gly Leu Leu Ala Gly Ser
1               5                   10                  15

Cys Ser Ala Ala
            20

<210> SEQ ID NO 59
<211> LENGTH: 20
<212> TYPE: PRT
<213> ORGANISM: Leishmania infantum

<400> SEQUENCE: 59

Ser Cys Ser Ala Ala Ala Glu Pro Ala Ala Ala Pro Ala Ala Pro
1               5                   10                  15

Ser Ala Ala Ala
            20

<210> SEQ ID NO 60
<211> LENGTH: 20
<212> TYPE: PRT
<213> ORGANISM: Leishmania infantum

<400> SEQUENCE: 60

Pro Ser Ala Ala Ala Lys Glu Glu Pro Glu Glu Ser Asp Glu Asp Asp
1               5                   10                  15

Phe Gly Met Gly
            20

<210> SEQ ID NO 61
<211> LENGTH: 20
<212> TYPE: PRT
<213> ORGANISM: Leishmania infantum

<400> SEQUENCE: 61

Ala Ala Lys Glu Glu Pro Glu Glu Ser Asp Glu Asp Asp Phe Gly Met
1               5                   10                  15

Gly Gly Leu Phe
            20

<210> SEQ ID NO 62
<211> LENGTH: 20
<212> TYPE: PRT
<213> ORGANISM: Leishmania infantum

<400> SEQUENCE: 62

Met Gln Tyr Leu Ala Ala Tyr Ala Leu Val Ala Leu Ser Gly Lys Thr
1               5                   10                  15

Pro Ser Lys Ala
            20

<210> SEQ ID NO 63
<211> LENGTH: 20
```

```
<212> TYPE: PRT
<213> ORGANISM: Leishmania infantum

<400> SEQUENCE: 63

Thr Pro Ser Lys Ala Asp Val Gln Ala Val Leu Lys Ala Ala Gly Val
1               5                   10                  15

Ala Val Asp Ala
            20

<210> SEQ ID NO 64
<211> LENGTH: 20
<212> TYPE: PRT
<213> ORGANISM: Leishmania infantum

<400> SEQUENCE: 64

Val Ala Val Asp Ala Ser Arg Val Asp Ala Val Phe Gln Glu Val Glu
1               5                   10                  15

Gly Lys Ser Phe
            20

<210> SEQ ID NO 65
<211> LENGTH: 20
<212> TYPE: PRT
<213> ORGANISM: Leishmania infantum

<400> SEQUENCE: 65

Glu Gly Lys Ser Phe Asp Ala Leu Val Ala Glu Gly Arg Thr Lys Leu
1               5                   10                  15

Val Gly Ser Gly
            20

<210> SEQ ID NO 66
<211> LENGTH: 20
<212> TYPE: PRT
<213> ORGANISM: Leishmania infantum

<400> SEQUENCE: 66

Leu Val Gly Ser Gly Ser Ala Ala Pro Ala Gly Ala Val Ser Thr Ala
1               5                   10                  15

Gly Ala Gly Ala
            20

<210> SEQ ID NO 67
<211> LENGTH: 20
<212> TYPE: PRT
<213> ORGANISM: Leishmania infantum

<400> SEQUENCE: 67

Ala Gly Ala Gly Ala Gly Ala Val Ala Glu Ala Lys Lys Glu Glu Pro
1               5                   10                  15

Glu Glu Glu Glu
            20

<210> SEQ ID NO 68
<211> LENGTH: 16
<212> TYPE: PRT
<213> ORGANISM: Leishmania infantum

<400> SEQUENCE: 68

Pro Glu Glu Glu Glu Ala Asp Asp Asp Met Gly Phe Gly Leu Phe Asp
1               5                   10                  15
```

```
<210> SEQ ID NO 69
<211> LENGTH: 20
<212> TYPE: PRT
<213> ORGANISM: Leishmania infantum

<400> SEQUENCE: 69

Met Ser Thr Lys Tyr Leu Ala Ala Tyr Ala Leu Ala Ser Leu Ser Lys
1               5                   10                  15

Ala Ser Pro Ser
            20

<210> SEQ ID NO 70
<211> LENGTH: 20
<212> TYPE: PRT
<213> ORGANISM: Leishmania infantum

<400> SEQUENCE: 70

Lys Ala Ser Pro Ser Gln Ala Asp Val Glu Ala Ile Cys Lys Ala Val
1               5                   10                  15

His Ile Asp Val
            20

<210> SEQ ID NO 71
<211> LENGTH: 20
<212> TYPE: PRT
<213> ORGANISM: Leishmania infantum

<400> SEQUENCE: 71

Val His Ile Asp Val Asp Gln Ala Thr Leu Ala Phe Val Met Glu Ser
1               5                   10                  15

Val Thr Gly Arg
            20

<210> SEQ ID NO 72
<211> LENGTH: 20
<212> TYPE: PRT
<213> ORGANISM: Leishmania infantum

<400> SEQUENCE: 72

Ser Val Thr Gly Arg Asp Val Ala Thr Leu Ile Ala Glu Gly Ala Ala
1               5                   10                  15

Lys Met Ser Ala
            20

<210> SEQ ID NO 73
<211> LENGTH: 20
<212> TYPE: PRT
<213> ORGANISM: Leishmania infantum

<400> SEQUENCE: 73

Ala Lys Met Ser Ala Met Pro Ala Ala Ser Ser Gly Ala Ala Ala Gly
1               5                   10                  15

Val Thr Ala Ser
            20

<210> SEQ ID NO 74
<211> LENGTH: 20
<212> TYPE: PRT
<213> ORGANISM: Leishmania infantum

<400> SEQUENCE: 74

Gly Val Thr Ala Ser Ala Ala Gly Asp Ala Ala Pro Ala Ala Ala Ala
1               5                   10                  15
```

-continued

```
Ala Lys Lys Asp
            20

<210> SEQ ID NO 75
<211> LENGTH: 21
<212> TYPE: PRT
<213> ORGANISM: Leishmania infantum

<400> SEQUENCE: 75

Ala Ala Lys Lys Asp Glu Pro Glu Glu Glu Ala Asp Asp Asp Met Gly
1               5                   10                  15

Phe Gly Leu Phe Asp
            20
```